United States Patent
Keefe et al.

(10) Patent No.: US 10,952,989 B2
(45) Date of Patent: Mar. 23, 2021

(54) SGLT1/2 INHIBITOR LIK066 FOR TREATING OBESITY

(71) Applicant: Novartis AG, Basel (CH)

(72) Inventors: Deborah Lynn Keefe, New Rochelle, NY (US); Qing Shao, Montville, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/490,554

(22) PCT Filed: Mar. 2, 2018

(86) PCT No.: PCT/IB2018/051350
§ 371 (c)(1),
(2) Date: Sep. 1, 2019

(87) PCT Pub. No.: WO2018/158744
PCT Pub. Date: Sep. 7, 2018

(65) Prior Publication Data
US 2020/0121639 A1    Apr. 23, 2020

Related U.S. Application Data

(60) Provisional application No. 62/466,572, filed on Mar. 3, 2017.

(51) Int. Cl.
*A61K 31/357* (2006.01)
*A61P 3/04* (2006.01)

(52) U.S. Cl.
CPC .............. *A61K 31/357* (2013.01); *A61P 3/04* (2018.01)

(58) Field of Classification Search
CPC ................................ A61K 31/357; A61P 3/04
See application file for complete search history.

(56) References Cited

U.S. PATENT DOCUMENTS

2013/0018005 A1*  1/2013  Bebernitz ................ A61P 3/10
514/23

FOREIGN PATENT DOCUMENTS

| WO | 2011/048112 A1 | 4/2011 |
| WO | 2012/140597 A1 | 10/2012 |

OTHER PUBLICATIONS

Novartis Pharmaceuticals: "A Study to Evaluate the change in Weight After 24 Weeks Treament With LIK066 in Obese or Overweight Adults", Apr. 1, 2017, [Retrieved from Internet on Mar. 29, 2018].
Novartis Pharmaceuticals: "Effect of LIK066 on Body Weight in Patients With Elevated Body Mass Index", May 12, 2017, [Retrieved from Internet on May 12, 2017].
NCT03100058 (https://clinicaltrials.gov/ct2/history/NCT03100058).
NCT02470403 (https://clinicaltrials.gov/ct2/history/NCT02470403).
NCT03320941 (https://clinicaltrials.gov/ct2/history/NCT03320941).

* cited by examiner

*Primary Examiner* — Umamaheswari Ramachandran
(74) *Attorney, Agent, or Firm* — Emily T. Wu; Novartis Institues for BioMedical Reseach, Inc.

(57) ABSTRACT

The present invention is drawn to methods for effecting weight loss, e.g. in the treatment of obesity and related conditions, including conditions associated with and/or caused by obesity per se.

15 Claims, 9 Drawing Sheets

FIGURE 1: Study Design
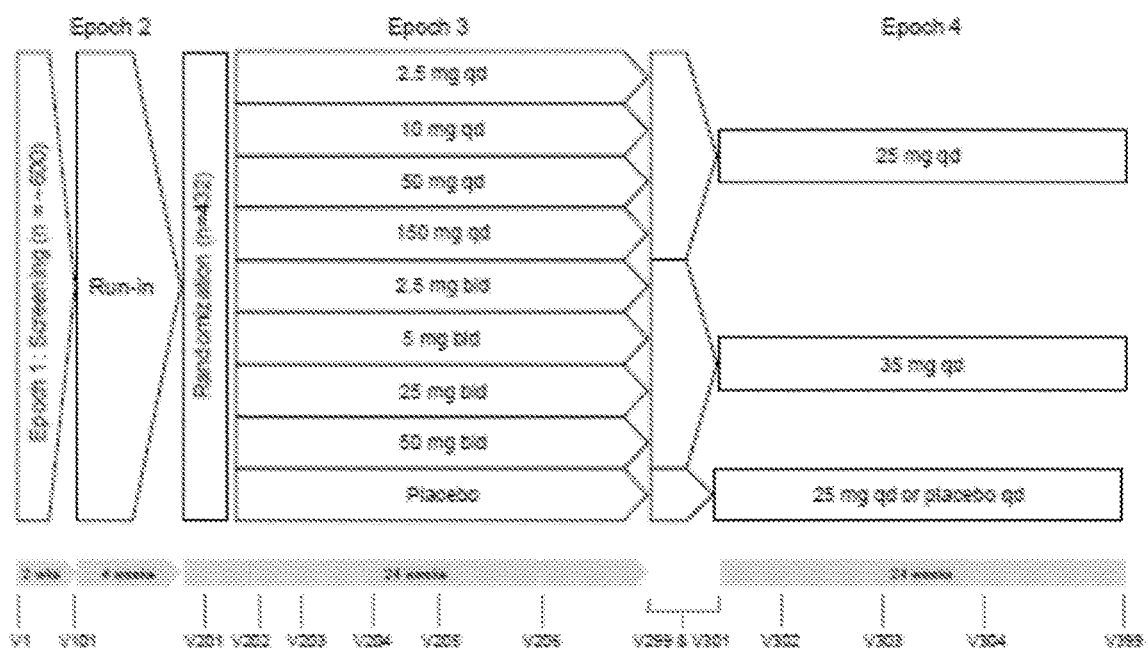

FIGURE 2: Assessment Schedule

| Epoch | 1 | 2 | 3 | | | | | | | 4 | | | 99*/TD/pSD/EOS |
|---|---|---|---|---|---|---|---|---|---|---|---|---|---|
| Visit | 1 Screening | 101 Run-in | 201 RAND/BL | 202 | 203 | 204 | 205 | 206 | 299/2001 | 302 | 303 | 304 | |
| Week | -6 | -4 | 0 | 2 | 4 | 6 | 12 | 18 | 24 | 28 | 34 | 40 | 40 |
| Screening assessments | | | | | | | | | | | | | |
| Informed consent | X | | | | | | | | | | | | |
| Randomization (Section 4) | X | | | | | | | | | | | | |
| Subject therapy aspects (Section 6.3) | X | | | | | | | | | | | | |
| Medical history | X | | | | | | | | | | | | |
| Medical history: previous suicidal events | X | | X | | | | | | | | | | |
| Smoking & alcohol history (Section 6.2) | X | | | | | | | | | | | | |
| Efficacy | | | | | | | | | | | | | |
| Height (Section 6.4.1) | X | X | X | X | X | X | X | X | X | X | X | X | X |
| Weight (Section 6.4.1) | X | X | X | | X | X | X | X | X | X | X | X | X |
| Waist circumference (Section 6.4.2) | | | X | | | X | | | X | | | X | X |
| SBP & DBP (Section 6.4.3) | X | | X | X | X | X | X | X | X | X | X | X | X |
| HbA1c (Section 6.4.3) | X | | X | | | X | X | X | X | X | X | X | X |
| FPG (Section 6.4.4) | X | | X | X | X | X | X | X | X | X | X | X | X |
| Fasting lipid profile (Section 6.4.5) | | | X | | | | | | X | | | X | X |
| hsCRP (Section 6.4.6) | | | X | | | | | | X | | | X | X |
| Patient reported outcomes | | | | | | | | | | | | | |
| APPADL (Section 6.5.1.1) | | | X | | | X | | | X | | | X | X |
| EQ-5D-5L (Section 6.5.1.1) | | | X | | | X | | | X | | | X | X |
| C-SSRS (Section 6.5.1.1) | | | X | | | X | | | X | | | X | X |
| Safety | | | | | | | | | | | | | |
| Complete physical examination (Section 6.6.1.1) | X | | | | | | | | | | | | X |
| Short physical examination (Section 6.6.1.1) | | | | | | | | | | | | | |

FIGURE 3: Assessment Schedule cont.

FIGURE 4: Assessment Schedule cont.

Figure 5: Power for detecting a significant dose response signal*

| Dose regimen | Effect size for best dose | SD | Average power** | Minimum power† |
|---|---|---|---|---|
| qd | 5 % | 5.5 % | 99.99 % | 99.96 % |
| | 5 % | 6.5 % | 99.71 % | 99.57 % |
| | 6 % | 5.5 % | 99.99 % | 99.99 % |
| | 6 % | 6.5 % | 99.99 % | 99.99 % |
| bid | 5 % | 5.5 % | 99.16 % | 95.84 % |
| | 5 % | 6.5 % | 96.50 % | 86.79 % |
| | 6 % | 5.5 % | 99.90 % | 99.43 % |
| | 6 % | 6.5 % | 99.28 % | 96.36 % |

* Assumes 432 subjects in UK006 and placebo arms with effective sample size of 367 subjects due to an effect of missing data equivalent to 15 % fewer subjects. Calculations were performed using the DoseFinding package in R.

Figure 6: Liver event and laboratory trigger definitions

| | Definitions/ threshold |
|---|---|
| Liver laboratory triggers | • 3 × ULN < ALT/AST ≤ 5 × ULN<br>• 1.5 × ULN < total bilirubin ≤ 2 × ULN |
| Liver events | • ALT or AST > 5 × ULN<br>• ALP > 2 × ULN (in the absence of known bone pathology)<br>• Total bilirubin > 2 × ULN (in the absence of known Gilbert syndrome)<br>• ALT or AST > 3 × ULN and INR > 1.5<br>• Potential Hy's law cases (defined as ALT or AST > 3 × ULN and total bilirubin > 2 × ULN [mainly conjugated fraction] without notable increase in ALP to > 2 × ULN)<br>• Any clinical event of jaundice (or equivalent term)<br>• ALT or AST > 3 × ULN accompanied by (general) malaise, fatigue, abdominal pain, nausea, or vomiting, or rash with eosinophilia<br>• Any AE potentially indicative of a liver toxicity (these events cover the following: hepatic failure, fibrosis and cirrhosis, and other liver damage-related conditions; the non-infectious hepatitis; the benign, malignant and unspecified liver neoplasms) |

Figure 7: Follow up requirements for liver events and laboratory triggers

| Criteria | Actions required | Follow-up monitoring |
|---|---|---|
| Potential Hy's law case* | • Discontinue the study treatment immediately<br>• Hospitalize, if clinically appropriate<br>• Establish causality<br>• Complete liver eCRF (see Section 7.3) | ALT, AST, total bilirubin, albumin, prothrombin time (PT)/international normalized ratio (INR), ALP and γ-GT until resolution¹ (frequency at investigator discretion) |
| ALT or AST | | |
| > 8 × ULN | • Discontinue the study treatment immediately<br>• Hospitalize if clinically appropriate<br>• Establish causality<br>• Complete liver eCRF (see Section 7.3) | ALT, AST, total bilirubin, albumin, PT/INR, ALP and γ-GT until resolution¹ (frequency at investigator discretion) |
| > 3 × ULN and INR > 1.5 | • Discontinue the study treatment immediately<br>• Hospitalize, if clinically appropriate<br>• Establish causality<br>• Complete liver eCRF (see Section 7.3) | ALT, AST, total bilirubin, albumin, PT/INR, ALP and γ-GT until resolution¹ (frequency at investigator discretion) |
| > 5 to ≤ 8 × ULN | • Repeat LFT within 48h<br>• If elevation persists, continue follow-up monitoring<br>• If elevation persists for more than 2 weeks, discontinue the study drug<br>• Establish causality<br>• Complete liver eCRF (see Section 7.3) | ALT, AST, total bilirubin, albumin, PT/INR, ALP and γ-GT until resolution¹ (frequency at investigator discretion) |
| > 3 × ULN | • Discontinue the study treatment | ALT, AST, total bilirubin, albumin, |

Figure 8: Follow up requirements for liver events and laboratory triggers cont.

| Criteria | Actions required | Follow-up monitoring |
|---|---|---|
| accompanied by symptoms[b] | immediately<br>• Hospitalize if clinically appropriate<br>• Establish causality<br>• Complete liver eCRF (see Section 7.3) | PT/INR, ALP and γ-GT until resolution[c] (frequency at investigator discretion) |
| > 3 to ≤ 5 × ULN (subject is asymptomatic) | • Repeat LFT within the next week<br>• If elevation is confirmed, initiate close observation of the subject | Investigator discretion<br>Monitor LFT within 1 to 4 weeks |
| ALP (isolated) | | |
| > 2 × ULN (in the absence of known bone pathology) | • Repeat LFT within 48h<br>• If elevation persists, establish causality<br>• Complete liver eCRF (see Section 7.3) | Investigator discretion<br>Monitor LFT within 1 to 4 weeks or at next visit |
| Total bilirubin (isolated) | | |
| > 2 × ULN (in the absence of known Gilbert syndrome) | • Repeat LFT within 48h<br>• If elevation persists, discontinue the study drug immediately<br>• Hospitalize if clinically appropriate<br>• Establish causality<br>• Complete liver eCRF (see Section 7.3) | ALT, AST, total bilirubin, albumin, PT/INR, ALP and γ-GT until resolution[c] (frequency at investigator discretion)<br>Test for hemolysis (eg. reticulocytes, haptoglobin, unconjugated [indirect] bilirubin) |
| > 1.5 to ≤ 2 × ULN (subject is asymptomatic) | • Repeat LFT within the next week<br>• If elevation is confirmed, initiate close observation of the subject | Investigator discretion<br>Monitor LFT within 1 to 4 weeks or at next visit |
| Jaundice | • Discontinue the study treatment immediately<br>• Hospitalize the subject<br>• Establish causality<br>• Complete liver eCRF (see Section 7.3) | ALT, AST, total bilirubin, albumin, PT/INR, ALP and γ-GT until resolution[c] (frequency at investigator discretion) |
| Any AE potentially indicative of a liver toxicity[d] | • Consider study treatment interruption or discontinuation<br>• Hospitalization if clinically appropriate<br>• Establish causality<br>• Complete liver eCRF (see Section 7.3) | Investigator discretion |

[a] Elevated ALT/AST > 3 × ULN and TBL > 2 × ULN but without notable increase in ALP to > 2 × ULN.
[b] (General) malaise, fatigue, abdominal pain, nausea, or vomiting, or rash with eosinophilia.
[c] Resolution is defined as an outcome of one of the following: (1) return to BL values, (2) stable values at three subsequent monitoring visits ≥ 2 weeks apart, (3) remain at elevated level after a max. of 6 months, (4) liver transplantation, and (5) death.
[d] These events cover hepatic failure, fibrosis and cirrhosis, and other liver damage-related conditions; the non-infectious hepatitis; the benign, malignant and unspecified liver neoplasms.

Figure 9: Specific renal alert criteria and actions

| Criteria | Action required |
|---|---|
| Serum event | |
| Serum creatinine increase 25 – 49 % compared to BL | Confirm 25 % increase after 24-48h<br>Follow up within 2-5 days |
| Acute kidney injury: serum creatinine increase ≥50 % compared to BL | Follow up within 24-48h if possible<br>Consider study treatment interruption<br>Consider subject hospitalization /specialized treatment |
| Urine event | |
| New dipstick proteinuria ≥ 1+<br>Albumin- or protein-creatinine ratio increase ≥2-fold<br>Albumin-creatinine ratio (ACR) ≥30 mg/g or ≥3 mg/mmol;<br>Protein-creatinine ratio (PCR) ≥150 mg/g or >15 mg/mmol | Confirm value after 24 to 48-h<br>Perform urine microscopy<br>Consider study treatment interruption / or discontinuation |
| New dipstick hematuria ≥ 1+ not due to trauma | Urine sediment microscopy<br>Perform serum creatinine, ACR |
| For all renal events | |
| Document contributing factors in the eCRF (see Section 7.4): co-medication, other co-morbidity conditions, and additional diagnostic procedures performed.<br>Monitor subject regularly (frequency at investigator's discretion) until either:<br>• event resolution: serum creatinine within 10 % of BL or protein-creatinine ratio within 50 % of BL, or<br>• event stabilization: serum creatinine level with ±10 % variability over last 6 months or protein-creatinine ratio stabilization at a new level with ±50 % variability over last 6 months. | |

SGLT1/2 INHIBITOR LIK066 FOR TREATING OBESITY

This application is a 371 U.S. national phase application of international application number PCT/IB2018/051350, filed 2 Mar. 2018, which claims the benefit of U.S. provisional application Ser. No. 62/466,572 filed 3 Mar. 2017; each of which is incorporated by reference herein in its entirety.

BACKGROUND OF THE INVENTION

Overweight and obesity represent a rapidly growing threat to the health of populations worldwide. Obesity raises the risk of morbidity from hypertension, dyslipidemia, type 2 diabetes mellitus (T2DM), coronary heart disease, stroke, gallbladder disease, osteoarthritis, sleep apnea and respiratory problems, and some cancers. Obesity is also associated with increased risk in all-cause and cardiovascular (CV) disease mortality. The risk is directly proportional to the degree of obesity in an individual, which is typically measured via the body to mass index, or BMI. BMI is typically measured in units of $kg/m^2$. For example, the risk of developing morbidity due to any of the above is especially high in individuals with a BMI of 25 or greater. The biomedical, psychosocial, and economic consequences of obesity have substantial implications for the health and well-being of the person with obesity.

Diet and behavior modification have been shown to be useful in producing effective, but modest weight loss leading to amelioration of comorbid medical problems. Addition of weight loss medications reinforces behavioral strategies; however clinical challenges remain with the magnitude of weight reduction (up to ~5% vs placebo) and the maintenance of the achieved weight loss. Some of the available treatments have limitations for long term use due to their gastro-intestinal (GI) adverse effects, others—due to central nervous system adverse effects. Therefore, there is a substantial opportunity and real need to develop weight loss medicines which will be more effective and better tolerated.

LIK066 is an inhibitor of the sodium-glucose co-transporter-1 (SGLT1) and sodium-glucose co-transporter-2 (SGLT2). The dual mechanism (renal and intestinal) to reduce re-absorption/absorption of glucose leads to loss of calories (calorie-loss enhancer). It also has the potential to reduce food intake via central mechanisms mediated by an increase in incretin hormones (glucagon-like peptide-1 (GLP-1) and peptide YY). In a Phase I study with normal and dysglycemic adults with BMI≥35 kg/m2, LIK066 150 mg once daily (qd) resulted in mean 5.7% placebo subtracted weight loss at 12 weeks. Although the weight loss effect of LIK066 is promising, over 90% of the participants in the study developed diarrhea as an adverse effect. This is a serious problem in its own right, as diarrhea can lead to serious health problems associated with dehydration, electrolytic imbalance, or malnutrition. It would be desirable to find a way to ameliorate or eliminate the serious side effect of diarrhea associated with administration of LIK066, The various embodiments of the present invention, described in more detail below, accomplish this objective through a novel method of administration of LIK to a patient in need.

SUMMARY OF THE INVENTION

The present invention provides a method of treating obesity and conditions associated herewith comprising administering to a patient in need, a daily oral dosage of LIK066, or salt thereof.

In another aspect of the invention, the invention is a method for effecting weight loss in a patient having a body mass index of at least 25 $kg/m^2$, comprising administering an unit dosage form comprising administering to a patient in need, a dosage of 1.0-200.0 mg of LIK066, or salt thereof.

BRIEF DESCRIPTION OF THE DRAWINGS

FIG. 1 provides a summary of the study design
FIG. 2 depicts the assessment schedule
FIG. 3 depicts the assessment schedule
FIG. 4 depicts the assessment schedule
FIG. 5 depicts power for detecting a significant dose response signal
FIG. 6 depicts liver event and laboratory trigger definitions
FIG. 7 depicts follow up requirements for liver events and laboratory triggers
FIG. 8 depicts follow up requirements for liver events and laboratory triggers
FIG. 9 depicts specific renal alert criteria and actions

DETAILED DESCRIPTION OF THE INVENTION

Definitions and Nomenclature

It must be noted that, as used in this specification and the appended claims, the singular forms "a," "an" and "the" include plural referents unless the context clearly dictates otherwise. Thus, for example, "an active agent" refers not only to a single active agent but also to a combination of two or more different active agents, "a dosage form" refers to a combination of dosage forms as well as to a single dosage form, and the like.

Unless defined otherwise, all technical and scientific terms used herein have the meaning commonly understood by one of ordinary skill in the art to which the invention pertains. Specific terminology of particular importance to the description of the present invention is defined below. When referring to an active agent, applicants intend the term "active agent" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds as will be discussed infra.

The terms "treating" and "treatment" as used herein refer to reduction in severity and/or frequency of symptoms, elimination of symptoms and/or underlying cause, and improvement or remediation of damage. In certain aspects, the term "treating" and "treatment" as used herein refer to the prevention of the occurrence of symptoms. In other aspects, the term "treating" and "treatment" as used herein refer to the prevention of the underlying cause of symptoms associated with obesity, excess weight, and/or a related condition. The phrase "administering to a subject" refers to the process of introducing a composition or dosage form of the invention into the subject (e.g., a human or other mammalian subject) via an art-recognized means of introduction.

By the terms "effective amount" and "therapeutically effective amount" of an agent, compound, drug, composition or combination of the invention which is nontoxic and effective for producing some desired therapeutic effect upon administration to a subject or patient (e.g., a human subject or patient).

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophilicity.

The term "effecting weight loss", "weight loss" or the like is meant to describe the weight loss from a base line at day 0 before administration of LIK066 of about 5% or more, or alternatively an amount of weight loss associated with a clinically beneficial reduction in one or more side effects associated with weight loss, or in a clinically beneficial reduction of the morbidity associated with one or more diseases that arise due to obesity, including but not limited to hypertension, dyslipidemia, T2DM, coronary heart disease, stroke, gallbladder disease, osteoarthritis, sleep apnea and respiratory problems.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, "subject" or "individual" or "patient" refers to any human subject for whom or which therapy is desired, and generally refers to the recipient of the therapy to be practiced according to the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

LIK066 is an inhibitor of the sodium-glucose co-transporter-1 (SGLT1) and sodium-glucose co-transporter-2 (SGLT2). LIK066 has the following chemical structure:

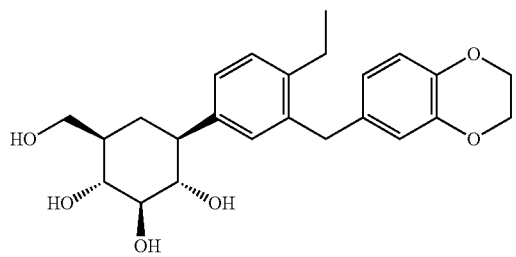 [SMILES: CCc1ccc([C@@H]2C[C@H](CO)[C@@H](O)[C@H](O)[C@H]2O)cc1Cc1ccc2c(c1)OCCO2]

LIK066 has the following IUPAC name: (2S,3R,4R,5S,6R)-2-(4-((2,3-dihydrobenzo[b][1,4]dioxin-6-yl)methyl)-4-ethylphenyl)-6-(hydroxymethyl)tetrahydro-2H-pyran-3,4,5-triol.

Methods of the Invention:

In a first embodiment, the invention is a method of treating obesity comprising administering to a patient in need, a dosage of 1.0-200.0 mg of LIK066, or salt thereof.

In a second embodiment, the invention is the method according to the first embodiment, wherein 2.5 mg of LIK066, or salt thereof, is administered.

In a third embodiment, the invention is the method according to first embodiment, wherein 5.0 mg of LIK066, or salt thereof, is administered.

In a fourth embodiment, the invention is the method according to the first embodiment, wherein 10.0 mg of LIK066, or salt thereof, is administered.

In a fifth embodiment, the invention is the method according to the first embodiment, wherein 25.0 mg of LIK066, or salt thereof, is administered.

In a sixth embodiment, the invention is the method according to the first embodiment, wherein 35.0 mg of LIK066, or salt thereof, is administered.

In a seventh embodiment, the invention is the method according to the first embodiment, wherein 50.0 mg of LIK066, or salt thereof, is administered.

In an eighth embodiment the invention is a method according to the first embodiment, wherein 150.0 mg of LIK066, or salt thereof, is administered.

In a ninth embodiment, the invention is the method according to any of the first through eighth embodiments, wherein the dosage is administered once a day.

In a tenth embodiment, the invention is the method according to any of the first through eighth embodiments, wherein the dosage is administered twice a day.

In an eleventh embodiment, the invention is the method according to any one of the first through tenth embodiments, wherein the administered dosage ameliorates the side effects of diarrhea.

In a twelfth embodiment, the invention is a method for effecting weight loss in a patient having a body mass index of at least 25 kg/m$^2$, comprising administering an escalating unit dosage form comprising administering to a patient in need, a dosage of 1.0-200.0 mg of LIK066, or salt thereof.

In a thirteenth embodiment, the invention is the method of any of the embodiments, wherein the subject has a body mass index between 25 kg/m$^2$ and 29.9 kg/m$^2$.

In a fourteenth embodiment, the invention is the method of any of the previous embodiments, wherein the subject has a condition associated with obesity.

In a fifteenth embodiment, the invention is the method of any of the previous embodiments, wherein the subject has a body mass index of at least 30 kg/m$^2$.

In a sixteenth embodiment, the invention is the method of the any of the previous embodiments, wherein the condition associated with obesity is selected from the group consisting of diabetes, elevated fasting blood glucose, insulin resistance, impaired glucose tolerance, pulmonary hypertension, asthma, shortness of breath, gallbladder disease, dyslipidemia, high cholesterol, high levels of triglycerides, osteoarthritis, reflux esophagitis, sleep apnea, menstrual irregularities, infertility, complications in pregnancy, gout, high blood pressure, hypertension, coronary artery disease, heart disease, muscular dystrophy, stroke, thrombotic stroke, deep vein thrombosis (DVT), migraines, metabolic disorders, hypoalphalipoproteinemia, familial combined hyperlipidemia, Syndrome X, insulin-resistant Syndrome X, colon cancer, rectal cancer, renal cancer, esophageal cancer, gallbladder cancer, pancreatic cancer, prostate cancer, breast cancer, uterine cancer, ovarian cancer, endometrial cancer, and cervical cancer.

In a seventeenth embodiment, the invention is the method of any of the previous embodiments, wherein the condition associated with obesity is selected from the group consisting of hypertension, dyslipidemia, and type 2 diabetes mellitus.

In an eighteenth embodiment, the invention is the method of any of the previous embodiments, wherein the condition associated with obesity is selected from the group consisting of high blood pressure, high levels of triglycerides, elevated fasting blood glucose, and diabetes.

In a nineteenth embodiment, the invention is the method of any of the previous embodiments, wherein the subject is suffering from at least two conditions associated with obesity selected from the group consisting of high blood pressure, high levels of triglycerides, elevated fasting blood glucose, and diabetes.

In a twentieth embodiment, the invention is the method of any of the previous embodiments, wherein the subject is suffering from at least two conditions associated with obesity selected from the group consisting of hypertension, dyslipidemia, and type 2 diabetes mellitus.

In a twenty-first embodiment, the invention is the method of the twelfth embodiment, wherein the escalating unit dosage form is formulated for oral administration.

In a twenty-second embodiment, the invention is the method of any of the previous embodiments, wherein the weight loss is effective to achieve a reduction of at least about 5% of body weight.

In a twenty-third embodiment, the invention is the method of any of the previous embodiments, wherein the LIK066 is formulated for sustained release, delayed release, or immediate release.

In a twenty-fourth embodiment, the invention is the method according to the twelfth embodiment, wherein 2.5 mg of LIK066, or salt thereof, is administered.

In a twenty-fifth embodiment, the invention is the method according to the twelfth embodiment, wherein 5.0 mg of LIK066, or salt thereof, is administered.

In a twenty-sixth embodiment, the invention is the method according to the twelfth embodiment, wherein 10.0 mg of LIK066, or salt thereof, is administered.

In a twenty-seventh embodiment, the invention is the method according to the twelfth embodiment, wherein 25.0 mg of LIK066, or salt thereof, is administered.

In a twenty-eighth embodiment, the invention is the method according to the twelfth embodiment, wherein 35.0 mg of LIK066, or salt thereof, is administered.

In a twenty-ninth embodiment, the invention is the method according to the twelfth embodiment, wherein 50.0 mg of LIK066, or salt thereof, is administered.

In a thirtieth embodiment, the invention is the method according to the twelfth embodiment, wherein 150.0 mg of LIK066, or salt thereof, is administered.

In a thirty-first embodiment the invention is the method according to any of the twelfth through thirtieth embodiments, wherein the dosage is administered once a day.

In a thirty-second embodiment, the invention is the method according to any of the twelfth through thirtieth embodiments, wherein the dosage is administered twice a day.

In a thirty-third embodiment, the invention is the method according to any one of the twelfth through thirtieth embodiments, wherein the administered dosage ameliorates the side effects of diarrhea.

In the thirty-fourth embodiment, the invention comprises LIK066 for use in the treatment of obesity comprising administering 1.0-200 mg of LIK066.

In the thirty-fifth embodiment, the invention is the invention of the thirty-fourth embodiment, wherein the patient to which LO=IK066 is administered has a body mass index of at least 25 kg/m$^2$.

In a thirty-fifth embodiment, the invention is the invention of the thirty-fourth or thirty-fifth embodiment, wherein 2.5 mg of LIK066, or salt thereof, is administered.

In a thirty-sixth embodiment, the invention is the invention of the thirty-fourth or thirty-fifth embodiment, wherein 5.0 mg of LIK066, or salt thereof, is administered.

In a thirty-seventh embodiment, the invention is the invention of the thirty-fourth or thirty-fifth embodiment, wherein 10.0 mg of LIK066, or salt thereof, is administered.

In a thirty-eighth embodiment, the invention is the invention of the thirty-fourth or thirty-fifth embodiment, wherein 25.0 mg of LIK066, or salt thereof, is administered.

In a thirty-ninth embodiment, the invention is the invention of the thirty-fourth or thirty-fifth embodiment, wherein 35.0 mg of LIK066, or salt thereof, is administered.

In a fortieth embodiment, the invention is the invention of the thirty-fourth or thirty-fifth embodiment, wherein 50.0 mg of LIK066, or salt thereof, is administered.

In a forty-first embodiment, the invention is the invention of the thirty-fourth or thirty-fifth embodiment, wherein 150.0 mg of LIK066, or salt thereof, is administered.

In the forty-second embodiment, the invention is the method according to any of the thirty-fourth though forty-first embodiments, wherein the dosage is administered once a day.

In a forty-third embodiment, the invention is the invention of the thirty-fourth though forty-second embodiments embodiment wherein the dosage is administered twice a day.

In a forty-fourth embodiment, the invention is the method of any of the thirty-fourth through forty-third embodiments, wherein the subject has a body mass index between 25 kg/m$^2$ and 29.9 kg/m$^2$.

In a forty-fifth embodiment, the invention is the method of any of the thirty-fourth though forty-fourth embodiments, wherein the subject has a condition associated with obesity.

In a forty-sixth embodiment, the invention is the method of any of the thirty-fourth though forty-fifth embodiments, wherein the subject has a body mass index of at least 30 kg/m$^2$.

In a forty-seventh embodiment, the invention is the method of the any of thirty-fourth though forty-sixth embodiments, wherein the condition associated with obesity is selected from the group consisting of diabetes, elevated fasting blood glucose, insulin resistance, impaired glucose tolerance, pulmonary hypertension, asthma, shortness of breath, gallbladder disease, dyslipidemia, high cholesterol, high levels of triglycerides, osteoarthritis, reflux esophagitis, sleep apnea, menstrual irregularities, infertility, complications in pregnancy, gout, high blood pressure, hypertension, coronary artery disease, heart disease, muscular dystrophy, stroke, thrombotic stroke, deep vein thrombosis (DVT), migraines, metabolic disorders, hypoalphalipoproteinemia, familial combined hyperlipidemia, Syndrome X, insulin-resistant Syndrome X, colon cancer, rectal cancer, renal cancer, esophageal cancer, gallbladder cancer, pancreatic cancer, prostate cancer, breast cancer, uterine cancer, ovarian cancer, endometrial cancer, and cervical cancer.

In a forty-eighth embodiment, the invention is the method of any of the thirty-fourth though forty-seventh embodiments, wherein the condition associated with obesity is selected from the group consisting of hypertension, dyslipidemia, and type 2 diabetes mellitus.

In an forty-ninth embodiment, the invention is the method of any of thirty-fourth though forty-eighth embodiments, wherein the condition associated with obesity is selected from the group consisting of high blood pressure, high levels of triglycerides, elevated fasting blood glucose, and diabetes.

In a fiftieth embodiment, the invention is the method of any of the thirty-fourth though forty-ninth embodiments, wherein the subject is suffering from at least two conditions associated with obesity selected from the group consisting of high blood pressure, high levels of triglycerides, elevated fasting blood glucose, and diabetes.

In a fifty-first embodiment, the invention is the method of any of the thirty-fourth though fiftieth embodiments, wherein the subject is suffering from at least two conditions associated with obesity selected from the group consisting of hypertension, dyslipidemia, and type 2 diabetes mellitus.

In a fifty-second embodiment, the invention is the method of any of the previous embodiments, wherein the weight loss is effective to achieve a reduction of at least about 5% of body weight.

In a fifty-third embodiment, the invention is the method of any of the previous embodiments, wherein the LIK066 is formulated for sustained release, delayed release, or immediate release.

In a fifty-fourth embodiment the invention is the method according to any of the previous embodiments, wherein the dosage is administered orally.

In a fifty-fifth embodiment, the invention is the method according to any of the previous embodiments, wherein the dosage is administered for at least 2 weeks.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

LIST OF ABBREVIATIONS

ACEi angiotensin-converting enzyme inhibitor
ACR albumin creatinine ratio
AE adverse event
ALT alanine aminotransferase
ANCOVA analysis of covariance
APPADL ability to perform physical activities of daily living
ARB angiotensin receptor blocker
AST aspartate aminotransferase
ATC anatomical therapeutic chemical classification system
AUC area under the curve
bid bis in die (twice a day)
BL baseline
BMI body mass index (kg·m-2)
BP blood pressure
β-hCG β-human chorionic gonadotropin
CDER center for drug evaluation and research
CFR US code of federal regulations
Cmax maximum concentration observed
CRO contract research organization
CV cardiovascular
CYP3A4 cytochrome P450 3A4
DBP diastolic blood pressure
DNA deoxyribonucleic acid
DPP-4 dipeptidyl-peptidase-4
DS&E drug safety & epidemiology
DSPP development safety profiling plan
ECG electrocardiogram
EDC electronic data capture
eCRF case report/record form (paper or electronic)
eGFR estimated glomerular filtration rate
ENR enrolled set
EQ5D-5L EuroQol 5 dimensions 5-level version EU European Union
FAS full analysis set
FDA Food & Drug Administration
FPG fasting plasma glucose
GCP good clinical practice
GI gastro-intestinal
GLP-1 glucagon-like peptide-1
GSRS gastrointestinal symptoms rating scale
HbA1c glycated hemoglobin A1c
HDL high density lipoprotein
hsCRP high sensitivity C-reactive protein
IB investigator brochure
ICF informed consent form
ICH International Conference on Harmonization of Technical Requirements for
Registration of Pharmaceuticals for Human Use
ID identification
IEC independent ethics committee
IN investigator notification
INR international normalized ratio
IRB institutional review board
IRT interactive response technology
LDL low density lipoprotein
LFT liver function test
LLOQ lower limit of quantification
LS least squares
MAR missing at random
MDRD modified diet in renal disease
MedDRA medical dictionary for regulatory activities
NOAEL no-observed-adverse-effect-level
NOEL no-effect-level
NYHA New York heart association
OAD oral anti-diabetic drug
PCR protein creatinine ratio
PK pharmacokinetics
PPS per-protocol set
PRO patient reported outcome
PT prothrombin time
qd quaque die (once daily)
SAE serious adverse event
SAF safety set
SBP systolic blood pressure
SD standard deviation
SGLT1 sodium-glucose co-transporter-1
SGLT2 sodium-glucose co-transporter-2
SU sulfonylurea
SUSAR suspected unexpected serious adverse reactions
T2DM type 2 diabetes mellitus
TD study treatment discontinuation
TG triglycerides
TSH thyroid stimulating hormone
UGE urinary glucose excretion
UGT uridine-5'-diphosphoglucoronosyltransferase
ULN upper limit of normal
US United States
UTI urinary tract infection
VLDL very low density lipoprotein
WBC white blood cell
WHO world health organization List of Terms Baseline (BL): Randomization (Visit 201) will be considered BL in this study.

Dosage: Dose of the study treatment given to the subject in a time unit (eg 25 mg once a day, 50 mg twice a day (bid), etc.).

Electronic data capture (EDC): EDC is the electronic acquisition of clinical study data using data collection systems, such as Web-based applications, interactive voice response systems and clinical laboratory interfaces. EDC includes the use of electronic case report forms (eCRFs) which are used to capture data transcribed from primary sources used at the point of care. End of study analysis: Statistical analyses performed at the end of the study including those specified in the statistical analysis plan and any data driven analyses that are performed at study end. The end of study analysis will take place after the last subject has completed Epoch 4 at Week 48.

Enrollment: Time of subject entry into the study at which the informed consent must be obtained (eg prior to starting any of the procedures described in the protocol). In this protocol, this will be at Visit 1 in Epoch 1.

Epoch: A portion of the study which serves a specific purpose. In this study, the 4 epochs are: screening, run-in, randomization & treatment, and follow-up.

eSource: eSource direct data entry refers to the capture of clinical study data electronically, at the point of care. eSource platform/applications reduce the use of paper capture source data during clinical visits. eSource combines source documents and case report forms into one application, allowing for the real time collection of clinical study information to sponsors and other oversight authorities, as appropriate.

Investigational drug: The drug of which the properties are being tested in the study; this definition is consistent with Unites States code of federal regulations (CFR) 21 Section 312.3 and is synonymous with "investigational new drug" or "investigational medicinal product". In this study, the investigational drug is LIK066.

Medication pack number: A unique identifier on the label of each investigational drug package.

Randomization number: A unique identifier assigned to each randomized subject, corresponding to a specific treatment arm assignment.

Rescue medication: Rescue medication is medication that can be used to treat those subjects with type 2 diabetes mellitus (T2DM) whose glycemic control is deteriorating. In this protocol a dipeptidyl-peptidase-4 (DPP-4) inhibitor or insulin should be used as rescue medication.

Run-in period: In this study, the run-in period is Epoch 2, where subjects who were successfully screened will receive placebo medication.

Source data/document: Source data refers to the initial record, document, or primary location from where data comes. The data source can be a database, a dataset, a spreadsheet or even hard-coded data, such as paper or eSource.

Study drug/treatment: Any single drug or combination of drugs administered to the subject as part of the required study procedures; includes investigational drug(s), placebo/comparator active drug run-ins or background therapy.

Study treatment discontinuation (TD): When the subject permanently stops taking study treatment prior to the defined study treatment completion date.

Subject identification (ID): A unique number assigned to each subject upon signing the informed consent form (ICF).

Variable: A measured value or assessed response that is determined in specific assessments and used in data analysis to evaluate the drug being tested in the study.

Week 24 Analysis: Statistical analyses performed at the end of Epoch 3 at Week 24 including those specified in the statistical analysis plan and any data driven analyses that are performed at Week 24. The Week 24 analysis will take place after the last subject has completed Epoch 3 at Week 24.

Withdrawal of consent: Withdrawal of consent from the study is defined as when a subject does not want to participate in the study any longer, and does not want any further visits or assessments, and does not want any further study related contact, and does not allow analysis of already obtained biologic material.

Example 1: A randomized, double-blind, dose-finding study to evaluate the change in weight after 24 weeks treatment with 8 doses of LIK066 compared to placebo in obese or overweight adults, followed by 24 weeks treatment with 2 doses of LIK066 and placebo.

Purpose and rationale: Evaluate the efficacy, tolerability and safety of LIK066 to support dose selection for Phase 3 development in overweight and obese adults.

Primary objective(s): To determine the dose-response signal and assess the dose-response relationship of two dose regimens of LIK066 as measured by the percent change from baseline (BL) in body weight relative to placebo after 24 weeks of treatment.

Secondary objectives: First: To assess the responder rates according to percent decrease in body weight either ≥5% or ≥10%, from BL at Week 24, for the overall population and each of the subgroups (normoglycemic subjects, dysglycemic subjects and subjects with type 2 diabetes mellitus (T2DM)).

Second: To assess the dose-response relationship for weight loss in normoglycemic subjects, dysglycemic subjects and subjects with T2DM after 24 weeks of treatment.

Third: To evaluate the effect of all LIK066 doses and regimens vs placebo for the overall population and by subgroups (normoglycemic subjects, dysglycemic subjects and subjects with T2DM) after 24 weeks of treatment on: Waist circumference; Change from BL in glycated hemoglobin A1c (HbA1c); Change from BL in fasting plasma glucose (FPG); Changes in systolic blood pressure (SBP) and diastolic blood pressure (DBP); Changes in the fasting lipid profile and high sensitivity C-reactive protein (hs-CRP); 24-h urinary glucose excretion (UGE) in a subset of subjects;

Fourth: To evaluate the change in weight and other efficacy parameters listed in the third secondary objective in the overall population and by subgroups by LIK066 treatment vs placebo between Week 24 and Week 48 (in Epoch 4).

Fifth: To evaluate safety (adverse events (AEs) and laboratory parameters) and tolerability of LIK066 over 24 weeks of treatment and over 48 weeks of treatment for all subjects.

Sixth: To evaluate AEs of interest and laboratory data in subjects treated with LIK066 or placebo between Week 24 and Week 48 (during Epoch 4).

Seventh: To evaluate 24-h urinary calcium and phosphorus excretion after 24 weeks of treatment and after 48 weeks of treatment in a subset of subjects.

Eighth: To evaluate the pharmacokinetics (PK) of LIK066.

Study design Multi-center, randomized, double-blind, parallel-group dose-finding study evaluating the effect on weight, tolerability and safety of LIK066 vs placebo. Following a screening visit, eligible subjects will enter the run-in. After the run-in period, eligible subjects will be randomized and will complete two periods of 24 weeks duration each. The total duration of the study is up to 54 weeks.

Population: Approximately 432 female and male subjects 18 and 75 years old.

Key inclusion criteria: Male and female, age 18 to 75 years old, both inclusive. Body mass index (BMI)≥30 kg/m2 or BMI≥27 kg/m2 combined with at least one obesity-related comorbidity (eg history of cardiovascular (CV) disease, hypertension, dyslipidemia, dysglycemia (pre-diabetes or T2DM), sleep-apnea syndrome). Agreement to comply with the study-required life-style intervention and treatment during the study.

Key exclusion criteria: Use of pharmacologically active weight-loss medications, glucagon-like peptide-1 (GLP-1) agonists or sodium-glucose co-transporter-2 (SGLT2) inhibitors within 3 months of screening, or between screening and randomization. Bariatric surgery. Lack of compliance with lifestyle intervention (defined as weight gain during the run-in (Epoch 2)), or with study medication (defined as <80% study drug intake during the run-in) assessed at randomization. Ketoacidosis, lactic acidosis, or hyperosmolar coma within 6 months of screening, or between screening and randomization. Symptomatic genital infection or urinary tract infection (UTI) in the 4 weeks prior to screening, or between screening and randomization.

Gastro-intestinal (GI) disorders associated with chronic diarrhea. Congestive heart failure, New York Heart Association (NYHA) class III or IV.

Study treatment: LIK066. Placebo.

Efficacy assessments: Body weight. Waist circumference. HbA1c. FPG. Blood pressure (BP). Fasting lipid profile and hsCRP. 24-h UGE in a subset of subjects.

Key safety assessments: Physical examinations; Vital signs; Monitoring of laboratory markers in blood and urine; Electrocardiogram; AE monitoring; and Liver & renal safety monitoring.

Other assessments: PK; Patient reported outcomes using ability to perform physical activities of daily living (AP-PADL), EuroQol 5 dimensions 5-level version (EQ5D-5L), gastrointestinal symptoms rating scale (GSRS); and AEs of special interest (hypoglycemia & ketoacidosis).

Data analysis The primary analysis of this study aims to detect a dose response signal for the percentage reduction in body weight after 24 weeks of treatment using data from all doses across the different dosing regimens (once daily (qd) and twice daily bid) to model the dose-response curve for each regimen and to provide sufficient information to choose the doses and dosing regimens for the further development of the drug. Hence, the following null and alternative hypotheses will be tested at a one sided significance level of 2.5%:

H01: there is no dose-response relationship for LIK066 given once daily (i.e. the dose response relationship is flat).

H11: there is a dose-response relationship for LIK066 given once daily (i.e. as dose increases, the percent weight decreases).

H02: there is no dose response relationship for LIK066 given twice daily (i.e. the dose response relationship is flat).

H12: there is a dose-response relationship for LIK066 given twice daily (i.e. as dose increases, the percent weight decreases).

The Multiple Comparison Procedure-Modeling methodology will be used to analyze the primary endpoint of percent change from BL in body weight at Week 24 in order to test these dose-response hypotheses and determine the dose-response relationship.

A set of the dose-response candidate models will be defined for each dosing regimen separately. In order to preserve the family-wise error rate at one-sided significance level of 2.5%, the optimal contrasts derived from the model candidate set for each dosing regimen will be individually compared to the critical value derived using a multiplicity adjustment accounts for all tests of comparing LIK066 doses to placebo across regimens simultaneously. The rejection of the null hypothesis for each dosing regimen will be achieved using the maximum test statistic in each dosing regimen from each estimated contrast test in the candidate set.

The analysis to derive the test statistics is based on an analysis of covariance (ANCOVA) model with the percent change in body weight from BL to Week 24 as a response variable, treatment (placebo and all LIK066 doses from each regimen), stratification factor of glycemic status at screening (dysglycemic, normoglycemic and T2DM) and pooled center/region as factors and BL weight as a covariate.

Model averaging approach will be used to estimate the dose-response in each dosing regimen separately. The primary analysis will be conducted on the full analysis set. Missing values of body weight at Week 24 will be imputed using the multiple imputation approach under a missing at random (MAR) assumption.

Study Objectives and Endpoints

Primary Objective

To determine the dose-response signal and assess the dose-response relationship of two dose regimens of LIK066 (2.5 mg, 10 mg, 50 mg and 150 mg qd, 2.5 mg, 5 mg, 25 mg and 50 mg twice daily (bid)) as measured by the percent change from baseline (BL) in body weight relative to placebo after 24 weeks of treatment.

Secondary Objective(s)

1. To assess the responder rates according to percent decrease in body weight either ≥5% or ≥10%, from BL at Week 24, for the overall population and each of the subgroups (normoglycemic subjects, dysglycemic subjects and subjects with T2DM.

2. To assess the dose-response relationship for weight loss in normoglycemic subjects, dysglycemic subjects and subjects with T2DM after 24 weeks of treatment.

3. To evaluate the effect of all LIK066 doses and regimens vs placebo for the overall population and by subgroups (normoglycemic subjects, dysglycemic subjects and subjects with T2DM after 24 weeks of treatment and between Week 24 and Week 48 on: Waist circumference; Change from BL in glycated hemoglobin A1c (HbA1c); Change from BL in fasting plasma glucose (FPG); Changes in systolic blood pressure (SBP) and diastolic blood pressure (DBP); Changes in the fasting lipid profile and high sensitivity C-reactive protein (hsCRP) and 24-h urinary glucose excretion (UGE) in a subset of subjects.

4. To evaluate the change in weight and other efficacy parameters listed in #3 in the overall population and by subgroups by LIK066 treatment vs placebo between Week 24 and Week 48.

5. To evaluate safety (adverse events (AEs) and laboratory parameters) and tolerability of LIK066 over 24 weeks of treatment and over 48 weeks of treatment for all subjects.

6. To evaluate AEs of interest and laboratory data in subjects treated with LIK066 25 mg qd, 35 mg qd or placebo between Week 24 and Week 48 (during Epoch 4).

7. To evaluate 24-h urinary calcium and phosphorus excretion after 24 weeks of treatment and after 48 weeks of treatment in a subset of subjects.

8. To evaluate the pharmacokinetics (PK) of LIK066.

Exploratory Objectives

1. To explore the effect of LIK066 on selected efficacy variables over 48 weeks in the individual Epoch 3/Epoch 4 treatment groups.

2. To explore the effect of LIK066 on selected AEs of interest and key laboratory parameters over 48 weeks in the individual Epoch 3/Epoch 4 treatment groups.

3. Health status assessed by patient reported outcomes.

Investigational Plan

Study Design

This is a multi-center, randomized, double-blind, parallel-group dose-finding study evaluating the effect on weight, tolerability and safety of 8 doses/regimens of LIK066 vs placebo (see FIG. 1). Following a screening visit (Visit 1) and a screening period of up to 2 weeks (Epoch 1), subjects meeting all eligibility criteria will enter the run-in Epoch 2 at Visit 101.

Epoch 2 (run-in)

Subjects meeting the eligibility criteria will enter the placebo run-in (Epoch 2). During the 4 weeks duration of Epoch 2, subjects will receive the placebo run-in medication.

At Visit 101, the subject's volume status must be assessed and hypovolemia must be corrected during the run-in in the elderly, in subjects with low SBP, or if on diuretics, angiotensin-converting enzyme inhibitors (ACEi) or angiotensin receptor blockers (ARBs).

At the start of Visit 101, all subjects will receive the following advice for lifestyle intervention (Look AHEAD Research Group 2013): Subjects with weight <114 kg (250 lbs.) will be advised to follow a 1200 to 1500 kcal/day diet; subjects with weight ≥114 kg (250 lbs.) will be advised to follow a 1500 to 1800 kcal/day diet. Consumption of 30% or fewer kcal from fat of which <10% kcal are from saturated fat will be recommended. Subjects will be advised to gradually increase their physical activity to reach a goal of 175 min of moderate intensity physical activity per week, preferably distributed over 5 days. Compliance with the lifestyle intervention shall be reviewed and re-enforced at every study visit.

Subjects with T2DM

Subjects with T2DM will continue their usual treatment, except for subjects taking sulfonylurea (SU) or insulin. These subjects may be at an increased risk of hypoglycemia due to the combination of the SU or insulin and weight loss, with or without consequent treatment with LIK066 in Epoch 3. Therefore: The dose of SUs for subjects with T2DM using such medication (either as monotherapy or in combination with other oral anti-diabetic drugs (OADs)) must be reduced by 50%, or as close to 50% as possible based on dose options available locally. In case of persistent deterioration in glycemic control, the concomitant background OAD should be initially escalated to the maximal approved dose, followed by addition of rescue medication when required. To limit the number of subjects with early deterioration of glycemic control who would meet the FPG rescue. For subjects on insulin, initial dose reduction of the total daily insulin dose by 10% or more may be considered at investigator's discretion based on subject's total daily dose and glycemic control. In case of deterioration in glycemic control, insulin can be up-titrated.

Epoch 3 (Treatment)

After the run-in Epoch 2, eligible subjects will be randomized in the ratio of 1:1:1:2:1:1:1:2:2 to one of the following regimes at Visit 201 (randomization): 2.5 mg qd LIK066; 10 mg qd LIK066; 50 mg qd LIK066; 150 mg qd LIK066; 2.5 mg bid LIK066; 5 mg bid LIK066; 25 mg bid LIK066; 50 mg bid LIK066; and Placebo.

At Visit 201, subjects will be randomized simultaneously to one of the nine Epoch 3 treatment schedules and to the subsequent treatment group/arm in Epoch 4 as follows:

Patients receiving one of the four LIK066 doses in the qd regimen in Epoch 3 will receive 25 mg qd in Epoch 4. Patients receiving one of the four LIK066 doses in the bid regimen in Epoch 3 will receive 35 mg qd in Epoch 4. Patients receiving placebo in Epoch 3 will either receive in a 1:1 ratio 25 mg qd or placebo in Epoch 4.

At randomization, subjects will be stratified according to their glycemic status at screening using the following criteria: Normoglycemic: no prior clinical diagnosis of T2DM, FPG <5.6 mM (100 mg/dL) and HbA1c <5.7% at Visit 1 (screening). T2DM: prior diagnosis of T2DM, or subjects without prior diagnosis of T2DM with HbA1c ≥6.5% and FPG ≥7.0 mmol/L (126 mg/dL) at Visit 1 (screening). Dysglycemic: all subjects not meeting criteria for normoglycemic or T2DM at Visit 1 (screening).

Figure 4:
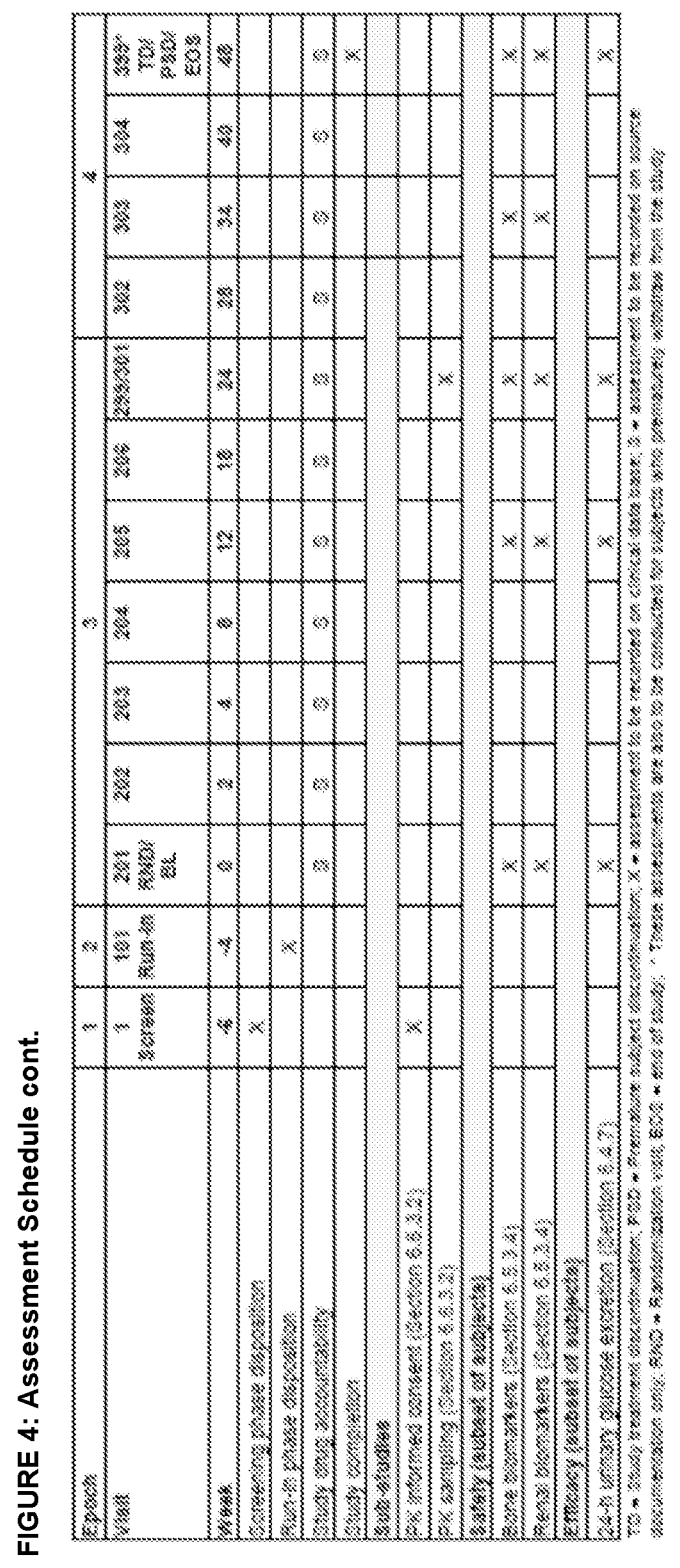

Following randomization, subjects will attend study visits in Epoch 3 (24 weeks) for assessment of efficacy, tolerability and safety parameters as defined in FIGS. 4-6. During Epoch 3, subjects will take the study medication. The doses of antidiabetic and antihypertensive medications should be adjusted in patients who, according to the investigator, could be at a safety risk (e.g. repetitive or severe hypoglycemia, symptoms and signs of volume depletion, etc.).

Epoch 4

After completing the procedures required at the last study visit of Epoch 3 (Visit 299), subjects in active study drug Epoch 3 arms will be switched to receive either LIK066 25 mg qd or LIK066 35 mg qd for another 24 weeks (see FIG. 1). The Epoch 3 placebo arm subjects will either continue the placebo treatment regimen or switch to LIK066 25 mg qd in a 1:1 ratio. Except for the placebo arm, the switch will results in 2 study groups, active drug 25 mg qd or 35 mg qd, in which longer-term safety, tolerability and efficacy of LIK066 following LIK066 treatment will be assessed.

The doses of antidiabetic and antihypertensive medications should be adjusted in patients who, according to the investigator, could be at a safety risk (e.g. repetitive or severe hypoglycemia, symptoms and signs of volume depletion, etc.).

PK Evaluation

Figure 3:
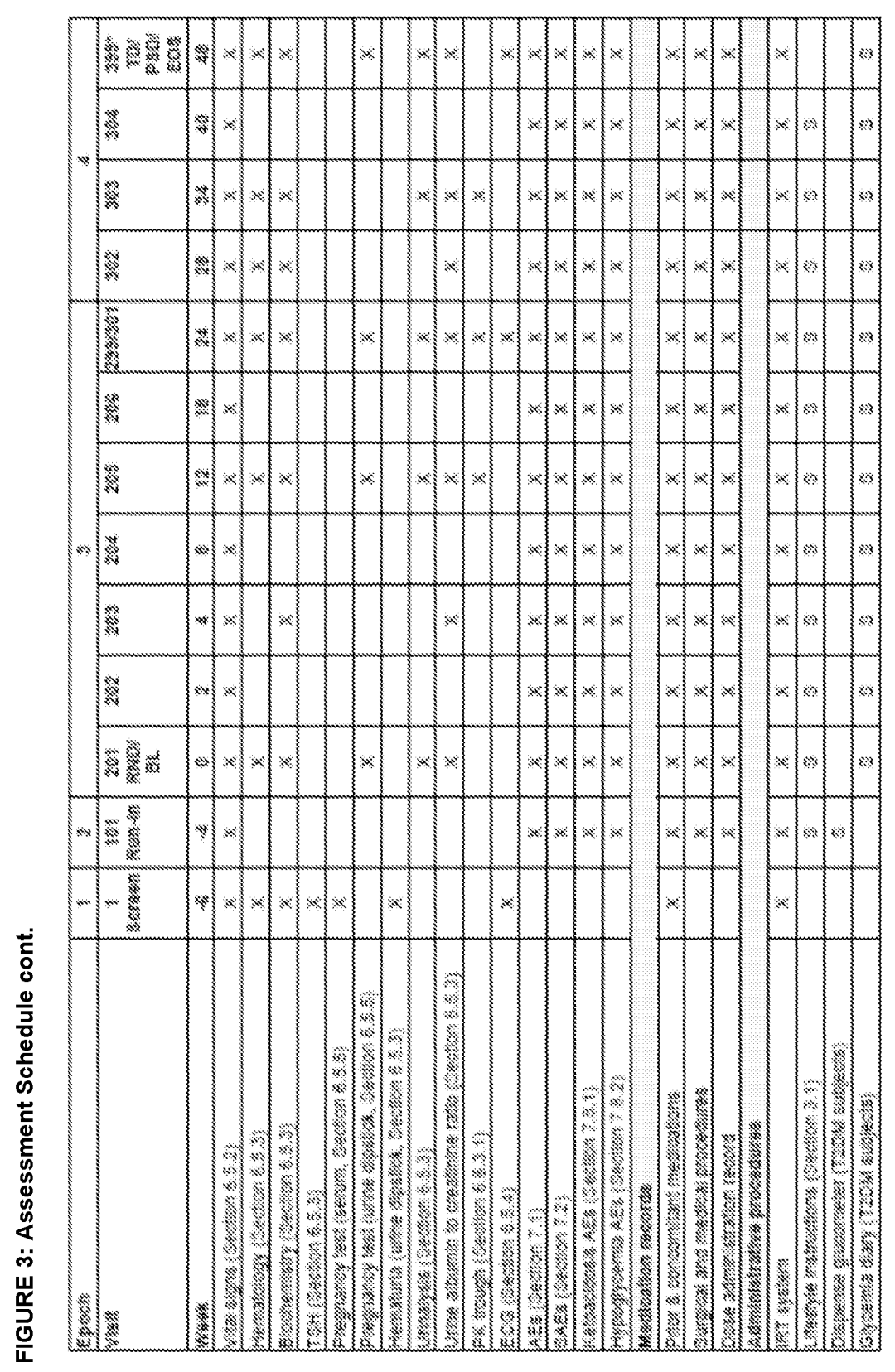

PK sampling will be performed at visits indicated in FIGS. 2-4.

Rationale for Study Design

The study is designed as a standard placebo-controlled, parallel-group study to obtain efficacy, tolerability and safety data in an unbiased fashion and determine the dose—response characteristics of the investigated drug. A single-blind placebo run-in period is included to facilitate the implementation of lifestyle measures, as well as assess the compliance with study treatment. Twenty-four weeks of treatment in Epoch 3 are considered sufficient to reach sub-maximal or maximal weight loss. The last 24 weeks of the study will provide information about the effect of two doses of LIK066 on weight, and also LIK066 safety and tolerability over a longer period (48 weeks). In addition to collection of trough PK samples in all subjects, PK sampling will be performed in a subset of subjects to enable characterization of the PK of LIK066 in the studied population and, if possible, from all tested doses and regimens in the study.

Rationale for Dose/Regimen, Route of Administration and Duration of Treatment

PK data with oral intake of LIK066 showed a sufficiently long half-life (approximately 16 h) to allow for once-daily LIK066 dosing. LIK066 150 mg qd was used in a Phase 1 study of 12 weeks duration, at a dose which is approximately 23 times below the safety margin for aneugenicity, and expected not to limit compliance due to GI effects. In this study, significant weight reduction of approximately 6% vs placebo was observed, but it was commonly associated with diarrhea events, predominantly mild, at a frequency which reduced over time in most subjects. Therefore a dose of 150 mg qd is selected as the highest qd dose in the current study. Twice daily dosing will be explored to evaluate whether increased frequency of LIK066 exposure in the intestines could result in greater weight loss and whether tolerability would be improved compared with same/similar total daily once daily dosings.

The eight active treatment regimens consist of four qd regimens and four bid regimens. The four qd regimens have been selected to cover one low dose (2.5 mg qd) at which some renal effect is present and no major gut effect is expected, two doses (10 mg qd and 50 mg qd) with sub-maximal/maximal renal and medium gut effect, and one qd dose (150 mg qd) with maximal renal and gut effects contributing to weight loss.

The four bid regimens have been selected to cover two low doses (2.5 mg and 5 mg bid) at which some renal effect is present and no major gut effect is expected, one dose (25 mg bid) with sub-maximal renal and medium gut effect, and one dose (50 mg bid) with maximal renal and gut effects contributing to weight loss.

Including both qd and bid dosing allows for thorough exploration of the LIK066 dose response curve of a drug with a dual mechanism of action (i.e. gut and renal).

During Epoch 4, subjects will receive 25 mg qd or 35 mg qd LIK066. These doses provide sub-maximal/maximal renal effect and a moderate gut effect and are expected to provide for good maintenance of the weight loss achieved in Epoch 3.

The oral route of administration has been chosen, as in previous studies, to ensure that active drug is present in the gut lumen.

Rationale for Choice of Comparator

A placebo group is a standard comparator in Phase 2 studies and is included to account for study effect and the lifestyle interventions.

Risks and Benefits

The risk to subjects in this study will be minimized by compliance with the eligibility criteria and study procedures, and close clinical monitoring. The potential risks of treatment with LIK066 are based in part on published reports on SGLT2 inhibition in humans. LIK066 administration in repeated dose preclinical safety studies up to 13 weeks in duration was associated with GI side effects in dogs (diarrhea) and rats (adaptive change of cecum with hypertrophy/hyperplasia) which is consistent with SGLT1 inhibition. Other findings included reversible weight loss, increased calcium excretion (rats and dogs), increase in trabecular bone formation (rats), and renal changes (mineralization and hyperplasia in rats) likely due to increased calcium absorption in the intestines. Adaptive, reversible changes in liver glycogen were present in both rats and dogs which were associated with changes in glucose utilization. Reversible decreases in red blood cell count were present in both rats (doses ≥30 mg/kg) and dogs (doses ≥5 mg/kg). The no-observed-adverse-effect level (NOAEL) was 5 mg/kg/day in rats and 0.5 mg/kg/day in dogs. In dogs, there was histological evidence of slight to moderate pyelonephritis in the mid and high dose groups, which was thought to be secondary to glucosuria and urinary catheterization for urine collection. No animals succumbed or required treatment for infection. Genotoxicity studies indicated that LIK066 is an aneugen i.e. a compound that produces aneuploidy (abnormal chromosome number) in dividing cells due to an effect on the spindle apparatus. There was no evidence in any assay that LIK066 directly damaged deoxyribonucleic acid (DNA).

Aneugenicity is a threshold event and does not pose a risk for genotoxicity as long as exposure remains below the threshold. LIK066 is not genotoxic at the 150 mg clinical dose which results in an exposure ~23 times below the threshold for aneugenicity. The highest selected LIK066 dose will maintain at least a 10 times safety margin relative to the exposures associated with the NOAEL for micronucleus induction.

In embryo-fetal development studies conducted in rats and rabbits, no teratogenicity was observed in either species. Embryo-fetal toxicity or lethality in the absence of maternal toxicity was not observed in either species. In both species the embryo-fetal no-effect-level (NOEL) was higher than the maternal NOEL, indicating that maternal toxicity preceded any adverse fetal effects.

Based on the results of embryo-fetal development studies in rats and rabbits and a fertility study in rats, LIK066 is not anticipated to increase the risk of adverse developmental effects. Women of child bearing potential must use basic contraception methods during the study. No such restriction exists for male subjects.

SGLT1 receptors are expressed in the heart, but their role is not well understood. In short term studies (up to 12 weeks) of LIK066 150 mg qd in obese subjects, including subjects with T2DM, LIK066 was safe and well tolerated; GI side effects (i.e. flatulence, diarrhea, predominantly mild) were reported. Publications on SGLT2 inhibition in subjects with T2DM treated with selective SGLT2 inhibitors reported higher incidences of urinary tract infections (UTIs) and genital mycotic infections compared with placebo.

SGLT2 inhibition may result in hypotension in elderly subjects, in subjects with low blood systolic pressure, or if on diuretics, ACEi, or ARB. Patients with T2DM treated with antidiabetic agents, especially with sulphonylurea or insulin may be at an increased risk of hypoglycemia, which can be more pronounced with significant weight loss. In rare cases treatment with SGLT2 inhibitors may be complicated by ketoacidosis. However, this has not been seen to date in clinical studies with LIK066. The only pre-clinical/class safety issues which have been seen in clinical studies with LIK066 are the GI side effects and genital and UTIs. A detailed description of safety and tolerability in humans with LIK066 is found in the LIK066 investigator brochure (IB).

Hematology and biochemistry tests will be monitored at each study visit after randomization and study drug can be discontinued for clinically significant laboratory change or abnormality as per investigator's judgment. Detailed criteria for follow-up in case of a liver event are defined in FIGS. 17-19. To prevent UTIs and genital infections, subjects will be instructed to pay attention to genital hygiene and have appropriate hydration. If UTI and/or genital infections occur, treatment will be initiated as appropriate at the investigator's discretion. Benefits to participation in the study may include weight reduction and, potentially, improvement in some cardio-metabolic markers such as blood pressure (BP), lipids or blood glucose.

Population

The study population will consist of male and female subjects. Approximately 432 subjects will be randomized at approximately 90 study sites. A screening failure rate of about 30% is expected; hence about 600 subjects will be screened.

Inclusion Criteria

Subjects eligible for inclusion in this study must fulfill all of the following criteria: 1. Written informed consent must be obtained before any assessment is performed; 2. Male and female, age 18 to 75 years old, both inclusive; 3. BMI≥30 kg/m2 or BMI≥27 kg/m2 combined with at least one obesity-related comorbidity (eg history of CV disease, hypertension, dyslipidemia, dysglycemia (prediabetes or T2DM), sleep-apnea syndrome); and 4. Agreement to comply with the study-required life-style intervention and treatment during the full duration of the study.

Exclusion Criteria

Subjects fulfilling any of the following criteria are not eligible for inclusion in this study. No additional exclusions may be applied by the investigator, in order to ensure that the study population will be representative of all eligible subjects: 1. Use of other investigational drugs within 5 half-lives of Visit 1 or within 30 days, whichever is longer; 2. History of hypersensitivity to any of the study drugs or their excipients or to drugs of similar chemical classes; 3. History or current diagnosis of electrocardiogram (ECG) abnormalities indicating significant risk of safety for subjects participating in the study such as: Concomitant clinically significant cardiac arrhythmias, eg, sustained ventricular tachycardia, and clinically significant second or third degree atrio-ventricular block without a pacemaker; and History of familial long QT syndrome or known family history of torsades de pointes; 4. Subjects taking medications prohibited by the protocol (see FIG. 3); 5. History of malignancy of any organ system (other than localized basal cell carcinoma of the skin or in situ cervical cancer), treated or untreated, within the past 5 years, regardless of whether there is evidence of local recurrence or metastases; 6. Pregnant or nursing (lactating) women; 7. Women of child-bearing potential, defined as all women physiologically capable of becoming pregnant, unless they are using basic methods of contraception during dosing of investigational drug. Basic contraception methods include: Total abstinence (when this is in line with the preferred and usual lifestyle of the subject). Periodic abstinence (e.g., calendar, ovulation, symptothermal, post-ovulation methods) and withdrawal are not acceptable methods of contraception; Female sterilization (have had surgical bilateral oophorectomy with or without hysterectomy), total hysterectomy or tubal ligation at least 6 weeks before taking investigational drug. In case of oophorectomy alone, only when the reproductive status of the woman has been confirmed by follow-up hormone level assessment; Male sterilization (at least 6 months prior to screening). For female subjects on the study, the vasectomized male partner should be the sole partner for that subject; Barrier methods of contraception: condom or occlusive cap (diaphragm or cervical/vault caps). For United Kingdom: with spermicidal foam/gel/film/cream/vaginal suppository; Use of oral, (estrogen and progesterone), injected or implanted hormonal methods of contraception or other forms of hormonal contraception that have comparable efficacy (failure rate <1%), for example hormone vaginal ring or transdermal hormone contraception or placement of an intrauterine device or intrauterine system. In case of use of oral contraception women should have been stable on the same pill for a minimum of 3 months before taking investigational drug; Women are considered post-menopausal and not of child bearing potential if they have had 12 months of natural (spontaneous) amenorrhea with an appropriate clinical profile (eg age appropriate, history of vasomotor symptoms) or have had surgical bilateral oophorectomy (with or without hysterectomy), total hysterectomy or tubal ligation at least 6 weeks ago. In the case of oophorectomy alone, only when the reproductive status of the woman has been confirmed by follow up hormone level assessment is she considered not of child bearing potential; 8. Use of pharmacologically active weight-loss medications, GLP-1 agonists or SGLT2 inhibitors within 3 months of Visit 1, or between Visit 1 and Visit 201 (randomization); 9. Bariatric surgery; 10. Lack of compliance with lifestyle intervention (defined as weight gain during Epoch 2), or with study medication (defined as <80% study drug intake during Epoch 2), assessed at Visit 201 (randomization); 11. Ketoacidosis, lactic acidosis, or hyperosmolar coma within 6 months of Visit 1, or between Visit 1 and Visit 201 (randomization); 12. Symptomatic genital infection or UTI in the 4 weeks prior to Visit 1, or between Visit 1 and Visit 201 (randomization); 13. GI disorders associated with chronic diarrhea; 14. Congestive heart failure, New York heart association (NYHA) class III or IV; 15. Myocardial infarction, stroke, surgery for heart disease, percutaneous coronary intervention in the 6 months prior to Visit 201 (randomization); 16. Unstable angina within 3 months of Visit 1, or between Visit 1 and Visit 201 (randomization); 17. Acute or chronic liver disease (except liver steatosis), such as hepatitis, cirrhosis or portal hypertension at Visit 1 or Visit 201 (randomization); 18. History of hepatitis B or C, or Hepatitis A or B vaccination in the last 3 months prior to Visit 1, or between Visit 1 and Visit 201 (randomization); 19. Active substance abuse, alcohol abuse (as defined by consumption of more than 24 alcohol units per week) or history of alcohol-related disease within the past 2 years; 20. Chronic treatment with medication which has a hepatotoxic potential; 21. Chronic use of anti-retroviral therapies; 22. Chronic use of strong cytochrome P450 3A4 (CYP3A4) inhibitors (eg clarithromycin, telithromycin, itraconazole, ketoconazole, voriconazole or posaconazole) or chronic use of strong uridine-5'-diphosphoglucoronosyltransferase (UGT) inhibitors (e.g. probenecid, valproic acid or mefenamic acid); 23. Concurrent medical conditions that may interfere with the interpretation of efficacy and safety data; 24. Clinically significant thyroid stimulating hormone (TSH) outside of the normal range at Visit 1; 25. HbA1c >10.0% at Visit 1 (screening); 26. FPG >13.3 mM (240 mg/dL) at Visit 201 (randomization); 27. Estimated glomerular filtration rate (eGFR, calculated via the modified diet in renal disease (MDRD) formula) <60 mL/min/1.73 m2 at Visit 1; 28. Alanine aminotransferase (ALT), or aspartate aminotransferase (AST) more than two-fold above upper limit of normal (ULN) (>2×ULN), or total bilirubin/direct bilirubin >1.5×ULN) at Visit 1, confirmed by repeat measurement within 5 working days of the respective visit; 29. Hemoglobin <12 g/L in men, <11 g/L in women at Visit 1 (screening); 30. Platelet count <100 000/µL and/or white blood cell (WBC) count <4000/µL at Visit 1 (screening); 31. Hematuria determined by dipstick measurement at Visit 1 (screening); 32. Elevated fasting triglycerides (TGs) >5.6 mM (500 mg/dL), at Visit 1 (screening), confirmed by repeat measurement within 3 working days of the respective visit; and 33. Clinically significant laboratory abnormalities which, in the opinion of the investigator, cause the subject to be considered inappropriate for inclusion in the study.

Treatment

Epoch 2 (Placebo run-in)

The sponsor will provide the following double-blind study medication for Epoch 2: LIK066 matching placebo tablets. All subjects will take 3 tablets in the morning and 2 tablets in the evening. The medication will be prepared for the placebo run-in in medication wallets.

Epoch 3 (Treatment)

The sponsor will provide the following double-blind study medication for Epoch 3: LIK066 2.5 mg tablets; LIK066 10 mg tablets; LIK066 25 mg tablets; LIK066 50 mg tablets; and LIK066 matching placebo tablets.

For each treatment arm subjects will receive a combination of the tablets described above. All subjects will take 3 tablets in the morning and 2 tablets in the evening, and the dose regimens will be prepared for each treatment arm in medication wallets.

Epoch 4

The sponsor will provide the following double-blind study medication for Epoch 4: LIK066 10 mg tablets; LIK066 25 mg tablets; and LIK066 matching placebo tablets. For each treatment arm in Epoch 4, subjects will receive a combination of the tablets described above to compose the 25 mg qd, 35 mg qd or placebo regimen. Subjects will take 2 tablets in the morning, and the dose regimens will be prepared for each treatment arm in medication wallets. No other drugs will be supplied. Sufficient medication will be supplied for treatment according to the study protocol.

Additional Treatment

No additional study treatment beyond investigational drug and placebo are included in this study.

Treatment Arms

All subjects entering Epoch 2 (run-in) will receive placebo. At Visit 201 (randomization), subjects eligible for randomization will be assigned 1:1:1:2:1:1:1:2:2 to one of the following treatment arms in Epoch 3: 2.5 mg qd LIK066 (approx. 36 subjects); 10 mg qd LIK066 (approx. 36 subjects); 50 mg qd LIK066 (approx. 36 subjects); 150 mg qd LIK066 (approx. 72 subjects); 2.5 mg bid LIK066 (approx. 36 subjects); 5 mg bid LIK066 (approx. 36 subjects); 25 mg bid LIK066 (approx. 36 subjects); 50 mg bid LIK066 (approx. 72 subjects); and Placebo (approx. 72 subjects).

At the end of Epoch 3, subjects from each of the four qd arms will enter Epoch 4 and will receive 25 mg qd LIK066. Subjects from each of the four bid arms in Epoch 3 will receive 35 mg qd LIK066 in Epoch 4. The subjects from the Epoch 3 placebo arm will receive placebo or 25 mg qd LIK066 in Epoch 4 in a 1:1 fashion.

Treatment Assignment and Randomization

At Visit 201 (randomization), all eligible subjects will be randomized via Interactive Response Technology (IRT) to one of the treatment arms for Epoch 3, and within that treatment arm to one of the regimens in Epoch 4. The investigator or his/her delegate will contact the IRT system after confirming that the subject fulfills all the inclusion/exclusion criteria. The IRT system will assign a randomization number to the subject, which will be used to link the subject to a treatment arm and will specify a unique medication number for the first package of study drug to be dispensed to the subject. The randomization number will not be communicated to the user. The randomization numbers will be generated using the following procedure to ensure that treatment assignment is unbiased and concealed from subjects and investigator staff. A subject randomization list will be produced by the IRT provider using a validated system that automates the random assignment of subject numbers to randomization numbers. These randomization numbers are linked to the different treatment arms, which in turn are linked to medication numbers. A separate medication list will be produced by or under the responsibility of Novartis drug supply management using a validated system that automates the random assignment of numbers to packs containing the investigational drug(s).

Randomization will be stratified into: Normoglycemic; T2DM; and Dysglycemic. Efforts will be made by close monitoring of the enrollment through the IRT system to ensure each of the three stratification sub-groups with at least 30% of total subjects enrolled in the study. The randomization scheme for subjects will be reviewed and approved by a member of the Novartis randomization office.

Treatment Blinding

Subjects, investigator staff and persons performing the assessments will remain masked to the identity of the treatment from the time of randomization until the final database lock, using the following methods: 1. Randomization data are kept strictly confidential until the time of unblinding, and will not be accessible by anyone else involved in the study with the following exceptions: the randomization codes associated with subjects from whom PK samples are taken will be disclosed to PK analysts who will keep the PK results confidential until database lock. 2. The identity of the treatments will be concealed by the use of study drug that are all identical in packaging, labeling, schedule of administration, appearance, taste and odor. Unmasking will only occur in the case of subject emergencies, at the time of Week 24 analysis and at the conclusion of the study.

The analysis group (statisticians/programmers), who will be unmasked to perform the Week 24 analysis, will not be involved in any study conduct activities related to the study Week 24 to Week 48 period (Epoch 4) after the unmasking. A separate analysis group, who does not have access to the analysis results and the identity of treatments at Week 24 analysis, will perform the pre-planned final analysis at the end of the study. The core study team (including the study leader(s), study physician and data manager), who are directly involved in study conduct activities during the study Week 24 to Week 48 period (Epoch 4), will not have access to the subject level data with identity of treatments such as subject listings at Week 24 analysis. The Week 24 analysis results and the identity of treatments will not be shared with the study site personnel until after the final database lock at the end of study.

Treating the Subject

Sponsor qualified medical personnel will be readily available to advise on study related medical questions or problems.

Subject Numbering

Each subject is uniquely identified by a subject number which is composed by the site number assigned by Novartis and a sequential number assigned by the investigator. Once assigned to a subject, a subject number will not be reused. Upon signing the informed consent form (ICF), the subject is assigned the next sequential number by the investigator. The investigator or his/her staff will contact the IRT system and provide the requested identifying information for the subject to register them into the IRT system. The site must select the case report/record form (paper or electronic) (eCRF) book with a matching subject number from the electronic data capture (EDC) system to enter data. If for any reason the subject fails to be treated with study medication after randomization, the IRT must be notified within 2 days that the subject was not treated. The reason for not being treated will be entered on the Screening Epoch (Epoch 1) Study Disposition eCRF.

Each subject is uniquely identified in the study by a combination of his/her center number and subject number. The center number is assigned by Novartis to the investigative site. Upon signing the informed consent form, the subject is assigned a subject number by the investigator. At each site, the first subject is assigned subject number 1, and subsequent subjects are assigned consecutive numbers (e.g. the second subject is assigned subject number 2; the third subject is assigned subject number 3). The investigator or his/her staff will contact the IRT system and provide the requested identifying information for the subject to register them into the IRT system. For studies using eCRFs, only the assigned subject number must be entered in the field labeled "Patient identification (ID)" on the EDC data entry screen (eg enter '1', '2', etc.). Once assigned to a subject, the subject number will not be reused. If the subject fails to be randomized for any reason, the IRT must be notified within 2 days that the subject was not randomized. The reason for not being randomized will be entered on the Screening Log, and the Demography eCRF must also be completed.

Dispensing the Study Drug

Each study site will be supplied by Novartis with study drug. The study drug packaging has a 2-part label. A unique number is printed on each part of this label which corresponds to one of the treatment arms. Investigator staff will identify the study drug package(s) to dispense to the subject by contacting the IRT system and obtaining the medication number(s). Immediately before dispensing the package to the subject, investigator staff will detach the outer part of the label from the packaging and affix it to the source document (drug label form) for that subject's unique subject number. All drug kits assigned by the IRT system will be recorded in the IRT database. Each study site will be supplied with study drug in packaging of identical appearance.

Handling of Study Treatment

Study treatment must be received by a designated person at the study site, handled and stored safely and properly, and kept in a secured location to which only the investigator and designees have access. Upon receipt, all study treatment must be stored according to the instructions specified on the labels. Clinical supplies are to be dispensed only in accordance with the protocol. Technical complaints are to be reported to the respective Novartis country pharma organization quality assurance department. Medication labels will be in the local language and comply with the legal requirements of each country. They will include storage conditions for the study treatment but no information about the subject except for the medication number. The investigator must maintain an accurate record of the shipment and dispensing of study treatment in a drug accountability log. Monitoring of drug accountability will be performed by monitors during site visits or remotely and at the completion of the study. Previously dispensed study medication wallets, including any remaining study medication, must be returned to the study center at each study visit and where applicable, at the time of discontinuation from study treatment.

At the conclusion of the study, and as appropriate during the course of the study, the investigator will return all unused study treatment, packaging, drug labels, and a copy of the completed drug accountability log to the Novartis monitor or to the Novartis address provided in the investigator folder at each site.

Instructions for Prescribing and Taking Study Treatment

The investigator should ensure that the subject clearly understands the dosing instructions outlined below. At Visit 101 (Epoch 2), each subject will be dispensed study drug wallets containing blisters with study medication. The blisters are constructed to easily deliver the daily required number of tablets for the morning dose and the tablets for the evening dose. The wallets contain sufficient medication for the run-in period of up to 4 weeks until Visit 201. From Visit 201 till Visit 299 (Epoch 3), subjects will be dispensed study drug wallets containing blisters with study medication. The blisters are constructed to easily deliver the daily required number of tablets for the morning dose and the tablets for the evening dose. The wallets contain sufficient medication for the time between each visit according to FIGS. 4-6. From Visit 301 till Visit 399 (Epoch 4), subjects will be dispensed study drug wallets containing blisters with study medication. The blisters are constructed to easily deliver the daily required number of tablets for the morning dose. The wallets contain sufficient medication for the time between each visit according to FIGS. 4-6.

In Epoch 2 and Epoch 3, subjects will be instructed to take 3 tablets LIK066 (or matching placebo) in the morning and 2 tablets in the evening, immediately before the meal. Study drug should be taken the same time throughout the study. In Epoch 4, subjects will be instructed to take 2 tablets LIK066 (or matching placebo) in the morning only, immediately before the meal. No study drug should be taken on the morning of a study visit; subjects with T2DM should not take their anti-diabetic treatment. Subjects should arrive in the fasting state; i.e. no food or drinks (except water) for a minimum of 8 h before the next scheduled visit. The study medication (and anti-diabetic medication, if applicable) will be taken after the completion of all study procedures for that visit prior to the first meal of the day (for subjects participating in the PK substudy). If the subject has not fasted for an adequate period of time, the collection of fasting laboratory evaluations must be rescheduled. The study drug regimen (and, if applicable, rescue medication) should not be taken prior to obtaining the fasting laboratory test samples. If a dose is missed and the subject realizes this within 4 h, the study drugs should be taken otherwise the subject should take the next scheduled dose. Previously dispensed study medication wallets, including any remaining study medication, must be returned to the study center at each study visit. All prescribed dosages and all dose changes during the study must be recorded on the appropriate study drug Dosage Administration Record eCRF(s). All kits of study treatment assigned by the IRT system will be recorded/ databased in the IRT system. During each study visit, the investigator should encourage compliance with study medication by instructing the subject to take the study drug exactly as prescribed to maintain the validity of the study and to optimize any potential effect of the study drug regimen. The subject should be instructed to contact the investigator if he/she is unable for any reason to take the study drug regimen as prescribed.

Permitted Dose Adjustments and Interruptions of Study Treatment

Investigational treatment dose adjustments and/or interruptions are not permitted.

Rescue Medication

During Epoch 3 and Epoch 4, rescue medication may be used in addition to ongoing study medication for those subjects with T2DM whose glycemic control is deteriorating. The subject must come in for an unscheduled visit to have a sample drawn for FPG & HbA1c measurement performed by the central laboratory if: Self-measured FPG on three consecutive occasions exceeds the limits in the following table:

TABLE 1

Rescue criteria for FPG or HbA1c (subjects with T2DM)

| Timeframe | Parameter | Value | Action |
|---|---|---|---|
| Between V201 (Randomization) and V204 (Week 8) | FPG | >240 mg/dL (13.3 mM) | Unscheduled visit for central laboratory parameter measurement. |
| Between V204 (Week 8) and V205 (Week 12) | FPG | >220 mg/dL (12.2 mM) | If elevation confirmed by central laboratory: background OAD to |
| Between V205 (Week 12) and V399 (Week 48) | FPG | >200 mg/dL (11.1 mM) | escalate to the maximum approved dose, followed by addition of another allowed OAD (eg a DPP-4 inhibitor |
| Between V205 (Week 12) and V399 (Week 48) | HbA1c | >8% | used according to the label or insulin as per the investigator's discretion) |

If the results confirm the exceeded limits, first the background OAD should be escalated to the maximal approved dose in steps if clinically indicated, followed by addition of rescue medication. Rescue medication, a dipeptidyl peptidase-4 (DPP-4) inhibitor or insulin, should be used according to the local label. Rescue medication must be provided locally. Rescued subjects will continue to participate in the study to allow for assessment of exposure and safety of LIK066. Use of rescue medication must be recorded on the Rescue Medication eCRF.

Concomitant Medication

The investigator must instruct the subject to notify the study site about any new medications they take after being enrolled into the study. All medications, procedures and significant nondrug therapies (including physical therapy and blood transfusions) administered after the subject was enrolled into the study must be recorded in the Concomitant Medications/Significant Non-Drug Therapies eCRF. Each concomitant medication must be individually assessed against all exclusion criteria and prohibited medications. If in doubt the investigator should contact the Novartis medical monitor before randomizing a subject or allowing a new medication to be started.

Prohibited Medication

Use of the treatments displayed the table below is not allowed after subjects have become eligible for participation into the study during the screening period. At the latest, subjects should stop using the medications listed at the start of Epoch 2. Some medications or products must be used with caution: Use of grapefruit juice (strong inhibitor of CYP3A4) should be discouraged and its consumption must not happen within 2 h of study medication intake. Use of antibiotic or antifungal medications that are strong inhibitors of CYP3A4 should be limited to 10 days during the study. Examples of such medications are clarithromycin, telithromycin, itraconazole, ketoconazole, voriconazole or posaconazole. Use of strong UGT inhibitors such as probenecid, valproic acid or mefenamic acid should be limited to 10 days during the study.

TABLE 2

Prohibited Medications

| Medication/product | Prohibition period | Action taken |
| --- | --- | --- |
| St. John's wort (strong CYP3A inducer) | Entire study | Discontinue prohibited medication during the screening period once subject is eligible for participation in the study |
| GLP-1 agonists | Entire study | Discontinue prohibited medication during the screening period once subject is eligible for participation in the study |
| SGLT2 inhibitors other than study medication | Entire study | Discontinue prohibited medication during the screening period once subject is eligible for participation in the study |
| Pharmacologically active weight-loss medication | Entire study | Discontinue prohibited medication during the screening period once subject is eligible for participation in the study |

Emergency Breaking of Assigned Treatment Code

Emergency code breaks must only be undertaken when it is required in order to treat the subject safely. Most often, study treatment discontinuation (TD) and knowledge of the possible treatment assignments are sufficient to treat a study subject who presents with an emergency condition. Emergency treatment code breaks are performed using the IRT system. When the investigator contacts the system to break a treatment code for a subject, the requested subject identifying information must be provided and the necessity to break the treatment code must be confirmed. The investigator will then receive details of the investigational drug treatment for the specified subject and a communication confirming this information. The system will automatically inform the Novartis monitor for the site and the study team that the code has been broken. It is the investigator's responsibility to ensure that there is a dependable procedure in p lace to allow access to the IRT system at any time in case of emergency. The investigator will provide the protocol number, the study drug name (if available) and the subject number. In addition, oral and written information to the subject must be provided on how to contact the investigator's backup in case of emergency, or when the investigator is unavailable, to ensure that un-masking can be performed at any time. Subjects whose treatment has been unmasked must be discontinued from the study treatment.

Study Completion and Post-Study Treatment

A subject will be considered to have completed the study when the subject has completed the last planned visit (see FIGS. 2-4). The study as a whole will be considered completed when all randomized subjects have completed the last visit planned in the protocol (see FIGS. 2-4) or have discontinued the study prematurely. For subjects who are loss to follow-up the investigator must provide follow-up medical care for all subjects who are prematurely withdrawn from the study, or must refer them for appropriate ongoing care.

Discontinuation of Study Treatment

Discontinuation of study treatment for a subject occurs when study drug is stopped earlier than the protocol planned duration, and can be initiated by the subject, the investigator or the sponsor. The investigator must discontinue study treatment for a given subject if, on balance, she/he believes that continuation would negatively impact the risk/benefit of study participation. Study treatment must be discontinued under the following circumstances: subject wish; pregnancy; use of prohibited treatment; any situation in which study participation might result in a safety risk to the subject; emergence of the following AE: ketoacidosis; any laboratory abnormalities that in the judgment of the investigator, taking into consideration the subject's overall status, prevents the subject from continuing participation in the study; subjects whose study treatment has been unmasked; and withdrawal of consent. If discontinuation of study treatment occurs, the subject should not be considered withdrawn from the study. The subject should return to the study site as soon as possible after discontinuation of study drug for a study treatment discontinuation visit (see FIGS. 2-4). TD visit assessments detailed in FIGS. 2-4 should be completed and recorded in the eCRF. The investigator must determine the primary reason for the subject's premature discontinuation of study treatment and record this information on the appropriate eCRF. After study treatment discontinuation, at a minimum, in abbreviated visits, the following data should to be collected at study site visits or via telephone contact: New and/or concomitant treatments and AEs/Serious AEs (SAEs).

If the subject cannot or is unwilling to attend any visit(s), the site staff should maintain regular telephone contact with the subject, or with a person pre-designated by the subject. This telephone contact should preferably be done according to the study visit schedule (FIGS. 2-4). The investigator must also contact the IRT system to register the subject's discontinuation from study treatment.

Withdrawal of Informed Consent

Subjects may voluntarily withdraw consent to participate in the study for any reason at any time. Withdrawal of consent from the study is defined as when all of the following apply: a subject does not want to participate in the study anymore; and does not want any further visits or assessments; and does not want any further study related contacts; and does not allow analysis of already obtained biologic material. In this situation, the investigator must make every effort (e.g. telephone, e-mail, letter) to determine the primary reason for the subject's decision to withdraw their consent and record this information. Study treatment must be discontinued and no further assessments conducted, and the data that would have been collected at subsequent visits will be considered missing. Further attempts to contact the subject in the context of the study are not allowed unless safety findings require communicating or follow-up. All efforts should be made to complete the assessments prior to study withdrawal. A final evaluation at the time of the subject's study withdrawal should be made as per FIGS. 2-4.

Loss to Follow-Up

For subjects whose status is unclear because they fail to appear for study visits without stating an intention to discontinue or withdraw, the investigator should show "due diligence" by documenting in the eSource system (where applicable) or the source documents steps taken to contact the subject, e.g. dates of telephone calls, registered letters, etc. A subject cannot be considered as loss to follow-up until the time point of their scheduled end of study visit has passed.

Early Study Termination by the Sponsor

The study can be terminated by Novartis at any time for any reason. This may include reasons related to the benefit risk assessment of participating in the study, practical reasons, or for regulatory or medical reasons (including slow enrollment). Should this be necessary, the subject must be seen as soon as possible and treated as a prematurely withdrawn subject. The investigator may be informed of additional procedures to be followed in order to ensure that adequate consideration is given to the protection of the subject's interests. The investigator will be responsible for informing the institutional review board (IRB)/independent ethics committee (IEC) of the early termination of the study.

Visit Schedule and Assessments

FIGS. 2-4 list all of the visits and assessments and indicate with an "X" when the assessments are performed. Subjects should be seen for all visits on the designated day, or as close to it as possible. Missed or rescheduled visits should not lead to automatic discontinuation. Subjects who prematurely discontinue the study for any reason should be scheduled for a visit as soon as possible, at which time all of the assessments listed for the final visit will be performed. At this final visit, all dispensed investigational product should be reconciled and the AE and concomitant medications reconciled on the eCRF. Subjects will be contacted for safety evaluations during the 30 days following the last administration of study treatment.

Information to be Collected on Screening Failures

All subjects who have signed the ICF but not entered into Epoch 3 will have the study completion page for the screening epoch, demographics, inclusion/exclusion, and SAE data collected. AEs that are not serious will be followed by the investigator and collected only in the source data.

Subject Demographics/other BL Characteristics

Demographic and BL characteristics data to be collected on all subjects include: date of birth, age, sex, race, ethnicity, source of subject referral, relevant medical history/current medical conditions present before signing informed consent including smoking and alcohol history. Where possible, diagnoses and notable symptoms will be recorded. Investigators will have the discretion to record abnormal test findings on the medical history eCRF whenever in their judgment, the test abnormality occurred prior to the ICF signature.

Treatment Exposure and Compliance

Compliance will be assessed by the investigator and/or study personnel at each visit using pill counts and information provided by the subject. This information should be captured in the source documents at each visit. All study treatment dispensed and returned must be recorded in the Drug Accountability Log. The site will also be required to complete the appropriate Dosage Administration Record eCRF to record any study drug regimen changes or interruptions.

On-Treatment Medication

For all medications (other than the study drug regimen) initiated after the start of study, the reason for prescribing the medication and the start and, where applicable, end dates will be recorded on the Concomitant Medications/Significant Non-Drug Therapies eCRF.

Rescue Medication

Information regarding the administration of rescue medication will be recorded on the appropriate eCRF.

Efficacy

Weight

Body weight will be measured to the nearest 0.1 kg at visits indicated in FIGS. 2-4 on a calibrated scale provided by the sponsor. The measurement will be performed with the study subject in underwear and without shoes. Voiding before weight measurement is required. Height will be measured at Visit 1 and will be used to calculate BMI.

Waist Circumference

Waist circumference will be measured to the nearest 0.1 cm at visits indicated in FIGS. 2-4 in a standing position, at the end of a normal expiration, using a tape at the level of the iliac crest.

HbA1c

HbA1c will be measured from a blood sample obtained at visits indicated in FIGS. 2-4 and analyzed using a National Glycohemoglobin Standardization Program certified method at a central laboratory.

FPG

FPG will be measured from a blood sample obtained after an overnight fast (at least 8 h after last evening food intake) at visits indicated in FIGS. 2-4 and analyzed at a central laboratory.

BP

Arterial BP, pulse rate readings and signs and symptoms of orthostasis will be assessed with an automated BP device. Three sitting BP measurements and one standing BP measurement will be performed at visits indicated in FIGS. 2-4. Every effort should be made to have the same staff member obtain BP measurements for a given subject, at the same time of day, using the same equipment, at each visit. Sitting BP and standing measurements must be performed prior to any procedure (e.g. blood draw) or medication intake. At Visit 1 (screening) BP must be measured at both arms. The arm with the higher SBP reading must be used for the BP measurements at Visit 1 and the same arm must be used at all subsequent visits. The arm used at each visit must be documented in the source documentation. The subject should be in a relaxed setting and measurements should not be taken immediately after exertion or the consumption of coffee. At each study visit, after the subject has been sitting for 5 minutes with the back supported and both feet placed on the floor, SBP and DBP will be measured three times using the automatic BP monitor and an appropriate size cuff. The bladder of the cuff should be large enough to encircle 80% of the arm. The cuff should be placed so its bottom is 1 to 2 cm above the elbow and the arm should be supported so that the bottom of the cuff is at the level of the heart. The tube should run down the center of the arm, approximately in line with the middle finger. The subject should be asked to relax his/her arm and turn the palm upward. The subject should not speak or move their arm during the measurement deflation of the cuff. Three separate sitting BP should be obtained with a full two-minute interval between measurements and with the cuff fully deflated between measurements. The subject will then stand, and after standing for two minutes, one BP measurement will be taken. All 3 sitting BP measurements and the single standing measurement will be recorded and documented in the eCRF and in the subject's source documents. All 3 sitting BP readings will be used for evaluation of sitting BP.

Fasting Lipid Profile & Inflammation Biomarkers

Fasting lipid profile, TG and hsCRP as described in FIGS. 2-4 will be measured on blood samples obtained after an overnight fast at visits indicated in FIGS. 2-4 and analyzed at a central laboratory.

24-h Urine Collection

UGE will be measured from 24-h urinary collection from subjects participating in the PK sub-study at visits indicated in FIGS. 2-4 and analyzed at a central laboratory. Results will not be communicated to the study sites or the sponsor to avoid unmasking. Urinary bone biomarkers (urinary calcium and phosphate excretion) will be measured from the same urine collection as well as urine albumin to creatinine ratio. Detailed instructions for urine collection will be provided to subjects, and handling of the urine sample will be described in the laboratory manual.

Appropriateness of Efficacy Assessments

Measurements of weight, waist circumference, HbA1c, FPG, BP and fasting lipids are standard measures to assess the efficacy of a weight loss drug and its effect on cardio-metabolic parameters. UGE measurement allows for evaluation of LIK066's primary mode of action's contribution to weight loss.

Safety

Physical Examination

A complete physical examination will be performed at visits indicated in FIGS. 2-4 and includes the examination of general appearance, skin, neck (including thyroid), eyes, ears, nose, throat, lungs, heart, abdomen, back, lymph nodes, extremities, vascular status, neurological status and volume status. If indicated based on medical history and/or symptoms, rectal, external genitalia, breast, and pelvic examinations will be performed. A short physical exam will include the examination of general appearance and assessments. They will be performed at all scheduled visits indicated in FIGS. 2-4 and at unscheduled study visits. Information for all physical examinations must be included in the source documentation at the study site. Clinically relevant findings that are present prior to signing the ICF must be included in the medical history part of the eCRF. Significant findings made after first administration of investigational drug which meet the definition of an AE must be recorded on the AE section of the eCRF.

Vital Signs

BP will be measured at visits indicated in FIGS. 2-4. The pulse rate from the last sitting BP measurement will be recorded. Respiratory rate will also be measured. Clinically notable vital signs deviations are noted as described in the table below.

TABLE 3

Vital Sign Deviation Parameters

| Vital sign | | Notable abnormalities |
|---|---|---|
| Pulse (beats/min) | | either ≥120 + increase ≥25* or >130 |
| | | either ≤50 + decrease ≥30* or <40 |
| BP (mm Hg) | systolic | either ≥180 + increase ≥30* or >200 |
| | | either ≤90 + decrease ≥30* or <75 |
| | diastolic | either ≥105 + increase ≥20* or >115 |
| | | either ≤50 + decrease ≥20* or <40 |

*Refers to post-BL value as compared to BL value.

Laboratory Evaluations

Laboratory evaluations for safety will be performed at visits indicated in FIGS. 2-4 and all specimens collected will be analyzed at a central laboratory. Details on the collection, shipment of samples, reporting of results by the central laboratory as well as laboratory notable range deviations are provided in the laboratory manual.

Hematology

Samples for analysis of hematology will be collected at visits indicated in FIGS. 2-4. Hematological measurements include: RBC, WBC, platelets, hematocrit, basophils, eosinophils, lymphocytes, monocytes and neutrophils.

Clinical Chemistry

Samples for analysis of clinical chemistry will be collected at visits indicated in FIGS. 2-4. Clinical chemistry measurements include TSH, Beta-HCG, ALT, albumin, ALP, AST, bicarbonates, bilirubin, BUN, calcium, chloride, creatinine, cystatin C, eGFR, magnesium, phosphates, potassium, total protein, sodium, uric acid, Gamma-GT, amylase, and lipase.

Urinalysis

Urine samples will be collected for analysis of parameters listed below at visits indicated in FIGS. 2-4. Urine will be used to assess pregnancy and hematuria (dipstick) at visits indicated in FIGS. 2-4 as well. Glucosuria results will not be communicated to the study sites or the Novartis study team to avoid unmasking. The tested parameters include: pH, specific gravity, total protein, glucose, ketones, nitrites, blood, leukocytes, hematuria, pregnancy, and the urine albumin: creatinine ratio.

Bone and Renal Biomarkers

Serum samples for bone and renal biomarkers will be collected at visits indicated in FIGS. 2-4 from subjects who participate in the PK sub-study. Urine samples for bone biomarkers will be collected. Biomarker analyses include Beta-C terminal telopeptide, cystatin, SP1NP, PTH, vitamin D2, vitamin D3, estradiol, osteocalcin, calcium, magnesium, phosphate, and the urinary cystatin C: creatine ratio.

ECG

ECGs must be recorded after 10 minutes rest in the supine position to ensure a stable ECG baseline. The preferred sequence of cardiovascular data collection during study visits is ECG collection first, followed by vital signs, and blood sampling. Single 12 lead ECGs are collected and interpreted by the principal investigator or their designee. The Fridericia QT correction formula should be used to assess the QT interval. Each ECG tracing must be labeled with study number, subject initials, subject number, date and time, and filed in the study site source documents. For any ECGs with subject safety concerns, two additional ECGs must be performed to confirm the safety. Clinically significant abnormalities must be recorded on the relevant section of the Medical History/Current Medical Conditions/AE eCRF(s) as appropriate.

Pregnancy and Assessments of Fertility

All pre-menopausal women who are not surgically sterile will have pregnancy testing. Additional pregnancy testing might be performed if requested by local requirements. A positive urine pregnancy test requires immediate interruption of study drug until serum β-human chorionic gonadotropin (β-hCG) is performed and found to be negative. If positive, the subject must be discontinued from the study treatment.

Appropriateness of Safety Measurements

The safety assessments are standard for this indication/subject population. The following additional assessments are included to document and evaluate risks identified with SGLT2 inhibitors or during the LIK066 clinical program: Bone biomarkers will evaluate the effect of LIK066 on bone re-modeling and Renal biomarkers will evaluate if LIK066 may cause kidney injury due to its dual SGLT1/2 inhibition.

Patient Reported Outcomes

The impact of LIK066 on the subject's daily living, self-perception and quality of life will be assessed by the following measures: Ability to perform physical activities of daily living (APPADL); EuroQoL 5 dimensions 5-level version (EQ5D-5L); and Gastrointestinal Symptom Rating Scale (GSRS). All questionnaires will be completed in the language most familiar to the respondent, at the scheduled study visits indicated in FIGS. 2-4 prior to the subject seeing the investigator for any clinical assessment or evaluation. The subject should be given sufficient instruction, space, time and privacy to complete the questionnaire. The study coordinator should check the responses to the questionnaire for completeness and encourage the subject to complete any missing responses. For paper eCRFs the original questionnaire will be kept with the subject's file as the source document. A detailed training manual relating to the administrative procedures of the questionnaires will be provided to the sites. Completed questionnaires will be reviewed and examined by the investigator, before the clinical examination, for responses that may indicate potential AEs or SAEs. The investigator should review not only the responses to the questions in the questionnaires but also for any unsolicited comments written by the subject. If AEs or SAEs are confirmed, then the investigator must record the events as per instruction.

PK Trough Sampling

PK trough sampling will be performed in all subjects at time-points indicated in FIGS. 2-4. At the morning of the visit, subjects must be in a fasting state.

PK Sub-Study

Subjects eligible for participation in the study will be invited to participate in the PK evaluation sub-study. In total, approximately 120 subjects will participate in the sub-study at selected study sites. PK sampling will be performed at visits indicated in FIGS. 2-4. At the morning of the visit, subjects must be in a fasting state. Blood samples will be collected at following time-points: 0 h (pre-dose) and approximately 1 h, 2 h, 4 h and 6 h post dose. After the first sample, the study medication will be administered followed by a standard meal. All samples will be assayed for LIK066 concentrations by Novartis or a designated contract research organization (CRO). PK sample matrix remaining after completion of the measurement may be used for exploratory assessment of metabolites or other bioanalytical purposes (e.g. cross check between different sites, stability assessment).

AEs

An AE is any untoward medical occurrence (e.g., any unfavorable and unintended sign including abnormal laboratory findings, symptom or disease) in a subject or clinical investigation subject after providing written informed consent for participation in the study until the end of study visit. Therefore, an AE may or may not be temporally or causally associated with the use of a medicinal (investigational) product. In addition, all reports of intentional misuse and abuse of the product are also considered an AE irrespective of whether a clinical event has occurred. The occurrence of AEs must be sought by non-directive questioning of the subject at each visit during the study. AEs also may be detected when they are volunteered by the subject during or between visits or through physical examination findings, laboratory test findings, or other assessments. Abnormal laboratory values or test results constitute AEs only if they fulfill at least one of the following criteria: They induce clinical signs or symptoms; they are considered clinically significant; and they require therapy. Clinically significant abnormal laboratory values or test results must be identified through a review of values outside of normal ranges/clinically notable ranges, significant changes from BL or the previous visit, or values which are considered to be non-typical in subjects with underlying disease. Investigators have the responsibility for managing the safety of individual subjects and identifying AEs. Alert ranges for selected laboratory and other test abnormalities are included in Table 3. AEs must be recorded in the AE eCRF under the signs, symptoms or diagnosis associated with them, accompanied by the following information: The severity grade: Mild: usually transient in nature and generally not interfering with normal activities. Moderate: sufficiently discomforting to interfere with normal activities. Severe: prevents normal activities. Its relationship to the study treatment: Yes or No. Its duration (start and end dates) or if the event is ongoing, an outcome of not recovered/not resolved must be reported. Whether it constitutes an SAE and which seriousness criteria have been met, all AEs must be treated appropriately. Treatment may include one or more of the following: no action taken (e.g. further observation only); investigational treatment dosage increased/reduced; investigational treatment interrupted/withdrawn; concomitant medication or non-drug therapy given; Non-drug therapy given; subject hospitalized/subject's hospitalization prolonged. Once an AE is detected, it must be followed until its resolution or until it is judged to be permanent, and assessment must be made at each visit (or more frequently, if necessary) of any changes in severity, the suspected relationship to the study drug, the interventions required to treat it, and the outcome. Any new information regarding the safety profile of the medicinal product that is identified will be communicated as appropriate, for example, via an investigator notification (IN) or an aggregate safety finding. New information might require an update to the informed consent and has then to be discussed with the subject. The investigator must also instruct each subject to report any new AE (beyond the protocol observation period) that the subject, or the subject's personal physician, believes might reasonably be related to study treatment. This information must be recorded in the investigator's source documents; however, if the AE meets the criteria of an SAE, it must be reported to Novartis.

Definition of SAE

An SAE is defined as any AE appearance of (or worsening of any pre-existing) undesirable sign(s), symptom(s) or medical conditions(s)) which meets any one of the following criteria: is fatal or life-threatening; results in persistent or significant disability/incapacity; constitutes a congenital anomaly/birth defect; and/or requires inpatient hospitalization or prolongation of existing hospitalization, unless hospitalization is for: routine treatment or monitoring of the studied indication, not associated with any deterioration in condition (specify what this includes).

Elective or pre-planned treatment for a pre-existing condition that is unrelated to the indication under study and has not worsened since signing the ICF. Social reasons and respite care in the absence of any deterioration in the subject's general condition which is medically significant, e.g. defined as an event that jeopardizes the subject or may require medical or surgical intervention. All malignant neoplasms will be assessed as serious under "medically significant" if other seriousness criteria are not met. Life-threatening in the context of a SAE refers to a reaction in which the subject was at risk of death at the time of the reaction; it does not refer to a reaction that hypothetically might have caused death if it were more severe (see Annex IV, ICH-E2D Guideline). Medical and scientific judgment should be exercised in deciding whether other situations should be considered serious reactions, such as important medical events that might not be immediately life threatening or result in death or hospitalization but might jeopardize the subject or might require intervention to prevent one of the other outcomes listed above. Examples of such events are intensive treatment in an emergency room or at home for allergic bronchospasm, blood dyscrasias or convulsions that do not result in hospitalization or development of dependency or abuse (see Annex IV, ICH-E2D Guideline). Any suspected transmission via a medicinal product of an infectious agent is also considered a serious adverse reaction.

SAE Reporting

To ensure subject safety, every SAE, regardless of causality, occurring after the subject has signed the ICF and until 30 days after the last study visit must be reported to Novartis within 24-h of learning of its occurrence. Any SAEs experienced after the 30 day period after the last study visit should only be reported to Novartis if the investigator suspects a causal relationship to study treatment. All follow-up information for the SAE including information on complications, progression of the initial SAE and recurrent episodes must be reported as follow-up to the original episode within 24-h of the investigator receiving the follow-up information. An SAE occurring at a different time interval or otherwise considered completely unrelated to a previously reported one must be reported separately as a new event. Information about all SAEs is collected and recorded on the SAE report form; all applicable sections of the form must be completed in order to provide a clinically thorough report. The investigator must assess the relationship of each SAE to each specific component of study treatment, complete the SAE report form in English, and submit the completed form within 24-h to Novartis. Detailed instructions regarding the submission process and requirements for signature are to be found in the investigator folder provided to each site. Follow-up information is submitted as instructed in the investigator folder. Each reoccurrence, complication, or progression of the original event must be reported as a follow-up to that event regardless of when it occurs. The follow-up information should describe whether the event has resolved or continues, if and how it was treated, whether the blind was broken or not, and whether the subject continued or withdrew from study participation. If the SAE is not previously documented in the IB (new occurrence) and is thought to be related to the study treatment a Novartis drug safety & epidemiology (DS&E) department associate may urgently require further information from the investigator for health authority reporting. Novartis may need to issue an IN to inform all investigators involved in any study with the same study treatment that this SAE has been reported. Suspected unexpected serious adverse reactions (SUSARs) will be collected and reported to the competent authorities and relevant ethics committees in accordance with European Union (EU) Guidance 2011/C 172/01 or as per national regulatory requirements in participating countries.

Liver Safety Monitoring

To ensure subject safety and enhance reliability in determining the hepatotoxic potential of an investigational drug, a standardized process for identification, monitoring and evaluation of liver events have to be followed. The following two categories of abnormalities and AEs have to be considered during the course of the study (irrespective of whether classified or reported as serious): Liver laboratory triggers, which will require repeated assessments of the abnormal laboratory parameter. Liver events, which will require close observation, follow-up monitoring and completion of the standard base liver eCRF pages. Please refer to FIGS. 7-8 for complete definitions of liver laboratory triggers and liver events. Every liver laboratory trigger or liver event as defined in FIG. 6 should be followed up by the investigator or designated personal at the study site as summarized below. Detailed information is outlined in FIGS. 7-8. For the liver laboratory trigger repeat the liver function test (LFT) within the next week to confirm elevation. These LFT repeats must be performed using the central laboratory if possible. If this is not possible, then the repeats can be performed at a local laboratory to monitor the safety of the subject. Repeat laboratory must then be performed at central laboratory as soon as possible. If a liver event is subsequently reported, any local LFTs previously conducted that are associated with this event must be reported on the Liver eCRF pages. If the elevation is confirmed, close observation of the subject will be initiated, including consideration of treatment interruption if deemed appropriate. For the liver events: Repeating the LFT to confirm elevation as appropriate; Discontinuation of the investigational drug if appropriate; Hospitalization of the subject if appropriate; A causality assessment of the liver event via exclusion of alternative causes (e.g., disease, co-medications); and an investigation of the liver event which needs to be followed until resolution. These investigations can include serology tests, imaging and pathology assessments, hepatologist's consultancy, based on investigator's discretion. All follow-up information, and the procedures performed must be recorded on appropriate eCRF pages, including the liver event overview eCRF pages.

Renal Safety Monitoring

The following two categories of abnormal renal laboratory values have to be considered during the course of the study: Serum event: Confirmed (after 24-h) increase in serum creatinine of 25% compared to BL during normal hydration status. Urine event: New onset 1+) proteinuria; confirmed by doubling in the urinary albumin: creatinine ratio. New onset 1+) hematuria. Every renal laboratory trigger or renal event as defined in FIG. 9 and be should followed up by the investigator or designated personnel at the study site as summarized in FIG. 9.

Reporting of Study Treatment Errors Including Misuse/Abuse

Medication errors are unintentional errors in the prescribing, dispensing, administration or monitoring of a medicine while under the control of a healthcare professional, subject or consumer (European Medicines Agency definition). Misuse refers to situations where the medicinal product is intentionally and inappropriately used not in accordance with the protocol. Abuse corresponds to the persistent or sporadic, intentional excessive use of a medicinal product, which is accompanied by harmful physical or psychological effects. Study treatment errors and uses outside of what is foreseen in the protocol will be collected in the Dose Administration Record eCRF irrespective of whether or not associated with an AE/SAE and reported to DS&E only if associated with an SAE. Misuse or abuse will be collected and reported in the safety database irrespective of it being associated with an AE/SAE.

Pregnancy Reporting

To ensure subject safety, each pregnancy occurring after signing the ICF must be reported to Novartis within 24-h of learning of its occurrence. The pregnancy should be followed up to determine outcome, including spontaneous or voluntary termination, details of the birth, and the presence or absence of any birth defects, congenital abnormalities, or maternal and/or newborn complications. Pregnancy must be recorded on the Pharmacovigilance Pregnancy Form and reported by the investigator to the local Novartis DS&E department. Pregnancy follow-up should be recorded on the same form and should include an assessment of the possible relationship to the study treatment. Any SAE experienced during the pregnancy and unrelated to the pregnancy must be reported on a SAE form.

AEs of Special Interest

Ketoacidosis

In rare cases, SGLT-2 inhibitors can lead to ketoacidosis. Therefore, investigators must pay close attention for any signs of ketoacidosis. Signs and symptoms of ketoacidosis may include deep and rapid breathing, nausea, vomiting, severe abdominal pain, confusion, unusual fatigue or sleepiness, and coma. All signs and/or symptoms and results from relevant laboratory tests must be reported on the AE eCRF. If ketoacidosis is confirmed, appropriate measures must be taken to correct the acidosis and monitor glucose levels. Every case of ketoacidosis must be reported to the Ketoacidosis adjudication committee, and the Ketoacidosis Adjudication eCRF must be completed.

Hypoglycemia

Patients with T2DM treated with anti-diabetic agents may be at an increased risk of hypoglycemia due to the expected weight loss. All patients with diabetes must be educated regarding hypoglycemic symptoms and treatment. This education should include general review of hypoglycemia: explanation of possible triggers of hypoglycemia (eg, strenuous exercise, delayed meals, changes in meal composition, illness, Ramadan-period, etc.); identification of the symptoms of hypoglycemia (eg, central symptoms such as dizziness, lightheadedness; adrenergic symptoms such as fast heart rate, palpitations, heart racing/pounding, shakiness; cholinergic symptoms such as sweating, hunger, blurred vision, impairment of motor function, confusion or inappropriate behavior); and review of appropriate treatment for events (oral glucose intake). The use of a home glucose monitor must be explained. A home glucose monitor will be provided with all appropriate supplies. Blood glucose should be measured each time the subject experiences symptoms which may be suggestive of hypoglycemia, as well as other time points as recommended by the investigator to inform about the need for reducing or discontinuing anti-diabetic treatment to prevent severe hypoglycemic events. Any time the subject experiences symptoms which they suspect are related to hypoglycemia, the subject should treat the event as appropriate. Subjects should record the event in the study diary, including: the glucose value; any relevant associated information, eg symptoms, precipitating factors (strenuous exercise, delayed or missed meals, changes in meal composition, illness, ramadan period, etc.); time of occurrence in relation to the last medication and to the last meal intake; the treatment used; the response to the treatment used. Additionally, if a subject performs routine self-monitoring of blood glucose, any asymptomatic plasma glucose <70 mg/dL (<3.9 mM) should be treated and recorded in the glycemia study diary and the subject must return the study diary at the next scheduled visit. Subjects without diabetes must have the symptoms of hypoglycemia explained and will be asked to report them at every study visit, if such occur. These subjects will not be provided with blood glucose meters or diaries.

Data Entry

The glycemia study diary will be reviewed by the investigator at each visit and any hypoglycemia must be recorded on the Hypoglycemic Events eCRF.

Data Review and Database Management

In this study, eSource is the data collection system intended to be used. The system allows electronic capture of source and study data as required per protocol. The eSource system replaces the need for using an eCRF. If it is not possible to use eSource for source data capture due to exceptional circumstances, data capture and data management will revert to other electronic methods as appropriate.

Site Monitoring

Before study initiation, at a site initiation visit or at an investigator's meeting, a Novartis representative will review the protocol and data capture requirements (i.e., eSource or eCRFs) with the investigators and their staff. During the study, Novartis employs several methods of ensuring protocol and good clinical practice (GCP) compliance and the quality/integrity of the sites' data. The field monitor will visit the site to check the completeness of subject records, the accuracy of data capture/data entry, the adherence to the protocol and to GCP, the progress of enrollment, and to ensure that study treatment is being stored, dispensed, and accounted for according to specifications. Key study personnel must be available to assist the field monitor during these visits. Continuous remote monitoring of each site's data may be performed by a centralized Novartis clinical research associate organization. Additionally, a central analytics organization may analyze data and identify risks and trends for site operational parameters, and provide reports to Novartis clinical teams to assist with study oversight.

The investigator must maintain source documents for each subject in the study, consisting of case and visit notes (hospital or site medical records) containing demographic and medical information, laboratory data, ECGs, and the results of any other tests or assessments. All information on eCRFs must be traceable to these source documents in the subject's file. The investigator must also keep the original ICF signed by the subject (a signed copy is given to the subject).

The investigator must give the monitor access to all relevant source documents to confirm their consistency with the data capture and/or data entry. Novartis monitoring standards require full verification for the presence of informed consent, adherence to the inclusion/exclusion criteria, documentation of SAEs, and of data that will be used for all primary variables. Additional checks of the consistency of the source data with the CRFs are performed according to the study-specific monitoring plan. No information in source documents about the identity of the subjects will be disclosed.

Data Collection

This study will incorporate technology (eSource) to capture source documents and source data electronically, consistent with final Food & Drug Administration (FDA) guidance (Center for drug evaluation and research (CDER) 2013) regarding electronic source and regulations related to the maintenance of adequate subject case histories (21 Code of Federal Regulations (CFR) 312.62 [b]). All electronic source documentation and data collected in this study will "meet the same fundamental elements of data quality (e.g., attributable, legible, contemporaneous, original, and accurate) that are expected of paper records" into a system that is fully validated and conforms to 21 CFR Part 11 requirements. Investigator site staff will not be given access to the system(s) until they have been appropriately trained. Study sites using eSource will be supplied with a tablet personal computer to directly record subject data and clinical observations on electronic forms with a similar look, feel, and behavior to paper forms. The system will permit the collection of both structured and unstructured information including ad-hoc comments, drawings, and relevant clinical notes the investigative site deems important. Information to be originally captured and reviewed electronically shall include details of the subject visit and the protocol required assessments performed as a part of these visits, medical history, and concomitant medications.

Certain data may be captured via other source documentation (such as safety laboratory data report, imaging) and then transcribed, uploaded or transferred into the eSource system. This, and any additional data treated in this manner, will be source data verified by the study field monitor per the monitoring plan and the location of source data (i.e., source, paper or a local electronic system) will be documented prior to study start in the Data Handling Plan. The eSource system has the ability to illustrate when a document has been entered from another source. When using an electronic source record as the original point of data capture, there is no additional data entry step for the site for data collected directly into the application; rather, the electronic source record directly populates the study database. Automatic validation programs check for data discrepancies and, by generating appropriate error messages, allow the data to be confirmed or corrected before transfer of the data to the vendor working on behalf of Novartis. Remote monitoring of the original electronic source records will take place, however on-site monitoring inspections will continue to take place in order to review data entry of source documentation directly captured on paper and transcribed into the system, to ensure protocol adherence, to assess site operational capabilities, and to perform other monitoring activities that cannot be performed remotely. The investigator must certify that the data entered into eSource are complete and accurate. After database lock, the investigator will receive copies of the subject data for archiving at the investigational site.

Database Management and Quality Control

The study will use electronic source documents and source data, and data entry will be done by the sites directly into eSource. Concomitant medications entered into the database will be coded using the world health organization (WHO) Drug Reference List, which employs the anatomical therapeutic chemical (ATC) classification system. Concomitant procedures, non-drug therapies and adverse events will be coded using the medical dictionary for regulatory activities MedDRA) terminology. Laboratory samples will be processed centrally and the results will be sent electronically to Novartis (or a designated CRO). Where applicable, diary data may be entered into an electronic diary by the subject or subjects will complete their patient reported outcome data on a site based tablet. The system will be supplied by a vendor(s), who will also manage the database. The database will be sent electronically to Novartis personnel (or designated CRO). Randomization codes and data about all study drug(s) dispensed to the subject and all dosage changes will be tracked using an IRT system. The system will be supplied by a vendor, who will also manage the database. The database will be sent electronically to Novartis (or a designated CRO). The occurrence of relevant protocol deviations will be determined. After these actions have been completed and the database has been declared to be complete and accurate, it will be locked and the treatment codes will be unblinded and made available for data analysis. Any changes to the database after that time can only be made after written agreement by Novartis Development management.

Adjudication Committee

A Ketoacidosis adjudication committee will review cases suspected for ketoacidosis as defined in the adjudication charter.

Data Analysis

The main analysis will be performed at the end of Epoch 3 when all subjects complete their treatment at Week 24 after randomization and data collected up to and including Week 24 (Visit 299) are cleaned (referred as "Week 24 analysis" in sections below). Data collected during Epoch 4 will be analyzed after the study ends, and will be presented in a separate report (referred as "End of study analysis" in sections below). For Week 24 analysis, the treatment groups presented are: LIK066 2.5 mg qd; LIK066 10 mg qd; LIK066 50 mg qd; LIK066 150 mg qd; LIK066 2.5 mg bid; LIK066 5 mg bid; LIK066 25 mg bid; LIK066 50 mg bid; Placebo; and Total (if applicable).

For End of study analysis, unless specified otherwise, the following treatment grouping strategy will be used, expressed as per the Epoch 3 treatment/Epoch 4 treatments a subject is assigned to at randomization: LIK066 qd any dose/LIK066 25 mg qd, shortened as LIK066/LIK066 25 mg qd; LIK066 bid any dose/LIK066 35 mg qd, shortened as LIK066/LIK066 35 mg qd; Placebo/LIK066 25 mg qd; Placebo/placebo, shortened as placebo; and Total (if applicable).

Analysis Sets

The following analysis sets will be used for the statistical analyses:

Enrolled set (ENR): all subjects who signed the ICF.

Full analysis set (FAS): the FAS comprises all subjects to whom study treatment has been assigned, except those who are not qualified for randomization but were inadvertently randomized into the study and did not take any study drug. Following the intent-to-treat principle, subjects will be analyzed according to the treatment assigned to at randomization.

Safety set (SAF): the SAF includes all subjects who received at least one dose of study medication. Subjects will be analyzed according to treatment received. Note that the safety set allows the inclusion of non-randomized subjects who received the study drug in error. The per-protocol set (PPS) is a subset of the FAS. It consists of all randomized subjects in the FAS who took at least one dose of study medication and have no major protocol deviations affecting the primary endpoint analysis. Major protocol deviations will be pre-specified prior to un-blinding treatment codes for analyses.

Subject Demographics and other BL Characteristics

Week 24 Analysis

The number of enrolled subjects, randomized subjects and screen failed subjects, as well as the number of subjects in each analysis set will be summarized. Demographics, BL characteristics, disease history and medical history will be summarized overall (total) and by treatment group for the FAS. Descriptive statistics (mean, Q1, median, Q3, standard deviation, minimum and maximum) will be presented for continuous variables for each treatment group and for all subjects (total). The number and percentage of subjects in each category will be presented for categorical variables for each treatment group and all subjects (total). Demographics and BL characteristics will be similarly summarized by the stratification factor (glycemic status at screening) as well.

End of Study Analysis

Demographics and other BL characteristics including medical history will be similarly summarized for FAS subjects who enter the study Week 24 to Week 48 period (Epoch 4) as for the Week 24 analysis.

Treatments

Week 24 Analysis

The duration of double-blind treatment exposure (days) in Epoch 3 will be summarized by treatment group both descriptively (i.e. mean, standard deviation, median, Q1 (25th percentile), Q3 (75th percentile), minimum and maximum) and by duration category for the safety set. The number and percentage of subjects receiving prior and concomitant medications will be summarized by treatment group and overall in SAF in separate tables according to the hierarchy levels of the WHO coding dictionary. Prior medications are defined as drugs taken and stopped prior to first dose of study medication. Any medication given at least once between the day of first dose of double-blind study medication and the end of Epoch 3 visit will be a concomitant medication, including those which were started pre-BL and continued into the treatment period.

The number and percentage of subjects meeting rescue criteria and taking rescue medication, and duration of exposure to rescue medication during Epoch 3 will be summarized by treatment group. The use of prohibited medication, if any, will also be summarized.

End of Study Analysis

The duration of overall treatment period (Epoch 3+Epoch 4) as well as the duration of Epoch 4 will be summarized by treatment group both descriptively and by duration-category for subjects in the SAF who enter the study Week 24 to Week 48 period (Epoch 4), respectively. Concomitant medications and rescue medications subjects take during Epoch 4 will be similarly summarized for subjects in SAF who enter Epoch 4.

Analysis of the Primary Variable(s)

Variable(s)

The primary analysis variable is the percent change in body weight (kg) from BL at Week 24. BL is defined as the last body weight value measured prior to or at the randomization visit (Visit 201). This analysis will be carried out on the FAS, with missing Week 24 values imputed.

Statistical Model, Hypothesis, and Method of Analysis

The objective of determination of a dose response signal and dose-response relationship in either qd or bid dosing regimen compared to placebo will be evaluated using an optimally weighted contrast test following the methodology described in Pinheiro J, Bornkamp B, Bretz F (2006) Design and analysis of dose finding studies combining multiple comparisons and modeling procedures. Journal of Biopharmaceutical Statistics; 16(5): 639-56. and Pinheiro J, Bornkamp B, Glimm E, et al (2014) Model-based dose finding under model uncertainty using general parametric models. Statistics in Medicine; 33(10): 1646-661.

To this end, a candidate model set is defined corresponding to the range of expected mean response in each of the dosing regimens. The candidate model set is used to generate a set of weights for the calculation of optimal contrasts between the responses in the studied dose groups and the placebo group. A statistical test comparing all doses in the different dosing regimens simultaneously to the control group is used, hence a multiplicity adjustment is applied that accounts for the multiple possible dose response behavior considered as well as the common placebo between the dosing regimens. A critical value is derived from a multivariate t-distribution using the correlation matrix induced by the correlations between the weights corresponding to the candidate sets as well as the correlation between the tests of shapes in the dosing regimens to the common placebo group.

Test of the Dose Response Signal

The null hypothesis of a flat dose-response relationship for the percentage reduction in body weight compared to placebo will be tested at a one-sided significance level of 2.5% against the alternative hypothesis of a dose-response relationship leading to a significant decrease in percent body weight. Hence, the following null and alternative hypotheses will be tested: H01: there is no dose-response relationship for LIK066 given qd (i.e., the dose response relationship is flat). H11: there is a dose-response relationship for LIK066 given qd (i.e., as dose increases, the percent weight decreases). H02: there is no dose response relationship for LIK066 given bid (i.e., the dose response relationship is flat). H12: there is a dose-response relationship for LIK066 given bid (i.e., as dose increases, the percent weight decreases). Given that we suspect the dose-response may behave differently between qd and bid regimens based on the data we have seen from the proof-of-concept study LIK066X2201, we define separate sets of the dose-response candidate models for each dosing regimen. In order to preserve the family-wise error rate at one-sided significance level of 2.5%, the optimal contrasts derived from the model candidate set for each dosing regimen will be individually compared to the critical value derived using a multiplicity adjustment accounts for all tests of comparing LIK066 doses to placebo across regimens simultaneously as described above. The rejection of the null hypothesis for each dosing regimen will be achieved using the maximum test statistic in each dosing regimen from each estimated contrast test in the candidate set. The candidate models generating the contrast weights are described in the table below, with the doses used to define parameters of interest being defined as total daily dose.

TABLE 4

Candidate dose-response models in consideration

| Table 9-1 # | Candidate models for qd regimen | Candidate models for bid regimen |
|---|---|---|
| 1 | $E_{max}$ model: $ED_{50}$ = 5 mg | $E_{max}$ model: $ED_{50}$ = 5 mg |
| 2 | $E_{max}$ model: $ED_{50}$ = 50 mg | $E_{max}$ model: $ED_{50}$ = 50 mg |
| 3 | Sigmoid $E_{max}$ $ED_{50}$ = 75 mg, H = 3.5 | Sigmoid Emax $ED_{50}$ = 75 mg, H = 3.2 |
| 4 | Sigmoid $E_{max}$ $ED_{50}$ = 25 mg, H = 0.7 | Linear log-dose null c = 0.8 |
| 5 | β-model α = 0.8 β = 0.2 scale = 180 | Linear |
| 6 | Exponential: λ = 125 | Quadratic δ = 0.007 |

The analysis to derive the test statistics is based on an analysis of covariance (ANCOVA) model with the percent change in body weight from BL to Week 24 as a response variable, treatment (placebo and all LIK066 doses from each regimen), stratum indicator (dysglycemic/normoglycemic/T2DM) and pooled center/region as factors and BL weight as a covariate. As needed, centers will be pooled according to country and region for the purpose of analysis. The response variable of percent change in body weight from BL to Week 24 used in the above ANCOVA is from an imputed dataset, where the missing Week 24 weight is imputed using the multiple imputation method. In order to account for the imputation uncertainty, this ANCOVA model will be repeated for each imputed dataset, which results in a set of least squares (LS) mean estimates for all dose groups for the two regimens and the related covariance matrices. Rubin's rule will be used to combine the multiple sets of LS mean estimates and the related covariance matrices to a single set of LS mean estimates of percent changes of body weight at Week 24 for all dose groups and the related covariance matrix.

The optimal contrasts derived from the candidate model sets will be applied to the combined estimated dose means and covariance matrix to obtain the t statistics for each candidate model in the two regimens and the common critical value C0.025. C0.025 is the common critical value derived from the reference multivariate t-distribution with the 12×12 correlation matrix induced by testing the candidate dose response models with respect to comparing all candidate models in both dosing regimens to the common placebo group. The intersection hypotheses H01 and H02 will be rejected and the statistical significance of dose-response in body weight reduction is established if the max (t1, t2, t3, t11, t12) C0.025. In other words, the intersecting null hypothesis requires the rejection of either H01 or H02.

Model Averaging to Obtain the Dose Responses for qd and Bid Dosing Regimens

The response data in each imputed data set, including relevant covariates, will be used to fit the models in the candidate set within each dosing regimen. The estimated dose-response in each dosing regimen will be derived by using model averaging methods on a subset of candidate models, for which the associated contrast tests are statistically significant. If there are more than three candidate models that are statistically significant, then only the top three candidate models with the largest test statistics will be selected. Model averaging will be carried out for each imputed data set, and the resulting mean efficacy estimates and confidence intervals will be derived using the combination variance that accounts for the uncertainty of the imputed data using Rubin's combination rules. Comparisons between LIK066 doses and placebo in each dosing regimen will be simultaneously derived for the model averaged estimates together with confidence intervals reflecting the imputation procedure applied. Target dose selection will be based on the model averaged dose response estimates of mean weight lowering efficacy of LIK066 over the dose range studied in the Phase 2B study.

Handling of Missing Values/Censoring/Discontinuations

Missing data for the primary endpoint will be imputed using a multiple imputation approach that assumes that the missingness mechanism can be retrieved from observed data (missing at random; MAR). The imputation model will include the longitudinal sequence of body weight data collected at each visit up to and including Week 24 visit and BL covariates (e.g. randomization stratification factor, FPG, age, gender, race), imputing missing visit observations for each dose group separately. The full detailed information about the multiple imputation algorithms will be specified in a separate statistical analysis plan.

Supportive Analyses

As a sensitivity analysis, the dose-response modeling will be conducted in the PPS as well. Results based on the single best dose response model fit will also be reported. Summary statistics for body weight will be presented by visit by treatment for observed and imputed values. The summary statistics n, mean, standard deviation (SD), median, minimum, maximum, Q1 and Q3 will be presented for the BL values and similarly for absolute values at and changes from BL to the post-BL visits. Figures will be produced to visually show the raw and the imputed mean changes by visit over 24 weeks of Epoch 3 for each treatment group, for all subjects and by strata separately.

Analysis of Secondary Variables

Variables

The following variables will be analyzed as well: responder rates based on percent decrease in body weight from BL at Week 24≥5%, or ≥10%; dose-response relationship in normoglycemic subjects, dysglycemic subjects and subjects with T2DM after 24 weeks of treatment; change from BL at Week 24 in waist circumference; change from BL at Week 24 in HbA1c; change from BL at Week 24 in FPG; change from BL at Week 24 in SBP and DBP; changes from BL at Week 24 in the fasting lipid profile (TG, total cholesterol, high density lipoprotein (HDL) cholesterol, low density lipoprotein (LDL) cholesterol, lipoproteins, calculated very low density lipoprotein (VLDL) cholesterol and non-HDL cholesterol) and hsCRP; change from BL at Week 24 in 24-h UGE.

Analysis Method: Responder Analysis

For the responder analysis, a logistic regression model will be performed using the percent decrease in body weight from BL at Week 24≥5% or ≥10% (yes/no) as a response variable, treatment, glycemic stratification factor and pooled center as fixed factors and BL body weight as a covariate, respectively. The Week 24 missing values will be imputed using the multiple imputation method. In order to account for the imputation uncertainty, this logistic regression model will be repeated for each imputed dataset, which results in a set of estimated odds ratio and its 95% confidence interval of an LIK066 dose vs placebo for all dose groups for the two regimens. Rubin's rule will be used to combine the multiple sets of odds ratios and 95% confidence intervals to a single set of odds ratio and its 95% confidence interval of an LIK066 dose vs placebo. Similar analysis by glycemic status stratification factor will be performed to assess the responder across each of the subgroups (normoglycemic subjects, dysglycemic subjects and subjects with T2DM). In addition, subjects meeting the predefined response criteria (percent decrease in body weight from BL at Week 24≥5% or ≥10%) will be summarized by treatment for all subjects and by glycemic stratification factor. A Cochran-Mantel-Haenszel-test will be performed to compare each qd or bid dose to the common placebo.

Analysis Method: Dose-Response Relationship by Glycemic Stratification Factor

For the dose-response relationship in normoglycemic subjects, dysglycemic subjects and subjects with T2DM, the dose-response modeling with the same candidate model sets for the primary variable will be performed on percent change of body weight from BL at Week 24 for these three subsets of subjects separately.

Analysis for other Secondary Endpoints

For changes from BL at Week 24 in HbA1c, FPG, SBP, DBP, waist circumference and 24-h UGE, a repeated measure ANCOVA model with treatment, visit, and treatment by visit interaction as fixed-effect factors and BL as a covariate, and a common unstructured covariance matrix among visits between treatments will be performed separately for each variable. The adjusted mean changes at Week 24 within each treatment, the differences in mean changes at Week 24 between the LIK066 and placebo treatments, and their 95% confidence intervals obtained from the above model will be presented. The analysis is based on likelihood method with an assumption of MAR for missing data.

In addition, a repeated measure ANCOVA model with treatment, visit, stratification factor (normoglycemic, dysglycemic, T2DM) and treatment by visit, treatment by stratification factor and treatment by visit by stratification factor interactions as fixed-effect factors and BL as a covariate, and a common unstructured covariance matrix among visits between treatments will be performed for the primary and secondary efficacy variables, respectively. The adjusted mean changes at Week 24 within each treatment, the differences in mean changes at Week 24 between the LIK066 and placebo treatments for each stratum, and their 95% confidence intervals obtained from the above models will be presented by strata for each efficacy endpoint. Similar repeated measure ANCOVA models will be performed for percent changes of lipid parameters and hsCRP from BL at Week 24. Summaries of absolute values and change from BL by treatment group and visit will be presented for all secondary efficacy variables for all subjects and by strata. Figures will be produced to visually show the raw mean changes by visit over 24 weeks of Epoch 3 for each treatment group, for overall and by strata separately. All analyses on secondary variables will be performed in the FAS.

End of Study Analysis

A repeated measure ANCOVA model with treatment, visit, the stratification factor, pooled center or region, and treatment by visit interaction as fixed-effect factors and BL as a covariate, and a common unstructured covariance matrix among visits between treatment will be performed separately for the changes from Week 24 to study end in each efficacy variable (body weight, FPG, HbA1c, SBP, DBP, lipid parameters, hsCRP, 24-h UGE and waist circumference). The adjusted mean changes from Week 24 to Week 48 within each treatment, the differences in mean changes from Week 24 to Week 48 between the LIK066 and placebo treatments, and their 95% confidence intervals obtained from the above models will be presented. The analysis is based on likelihood method with an assumption of MAR for missing data. A similar repeated measure ANCOVA model with additional glycemic stratification factor by treatment interaction and treatment by visit by stratification factor interaction terms will be performed to assess the body weight change from Week 24 to study end across each of the subgroups (normoglycemic subjects, dysglycemic subjects and subjects with T2DM). The p-value for the interaction of treatment by stratification factor at Week 24 will be calculated from this model as well. Note that for lipid parameters, the percent changes (instead of absolute change) from Week 24 to study end will be used as a response variable in the above repeated measure ANCOVA model.

Summaries of absolute values and changes (and/or percent changes for body weight and lipid parameters) from Week 24 by treatment group and visit will be presented for all efficacy variables, for all subjects and by stratification strata, respectively. Changes from BL will be similarly summarized as well. Figures will be produced to visually show the raw mean changes by visit over entire study period of 48 weeks for each treatment group. All analyses will be performed in subjects in the FAS who enter Epoch 4.

Safety Variables

Week 24 Analysis

All safety analyses will be performed in the SAF.

AEs

Treatment emergent AEs will be summarized. A treatment-emergent AE is defined as any AE that develops after initiation of the study treatments or any event already present that worsens following exposure to the study treatment. The number and percentage of subjects having AEs will be presented by treatment group and different hierarchy levels of the MedDRA coding dictionary. Summaries will also be presented by greatest severity, for AEs suspected to be related to study drug, serious AEs, AEs leading to discontinuation, to dosage adjustment, to death and other significant AEs. The hypoglycemic events will be similarly summarized. Further information related to hypoglycemic events (eg if third party assistance required, was medical assistance received, etc.) may be provided as well. AEs related to identified and potential risks as specified in the development safety profiling plan (DSPP) will be summarized and presented separately. The frequencies and percentages of the adjudication confirmed ketoacidosis events will be provided by treatment. In addition, for selected AEs including hypotension, hypoglycemia, hyperkalemia, diarrhea, and genital and UTI, a by-stratification factor of BL glycemic status subgroup analysis will be provided.

Laboratory Data, Vital Signs, ECG and Bone Markers

Descriptive summary statistics including for the change from BL to each study visit up to and including Week 24 visit will be presented by treatment group for each laboratory parameter, as well as for the maximum change from BL. In addition, shift tables will be provided for all parameters with available ranges to compare a subject's BL laboratory evaluation relative to the most extreme post-BL value. For the shift tables, normal ranges as well as specifically defined clinically notable/abnormality limits, if available—will be used. The vital sign and ECG data collected during Epoch 3 will be descriptively summarized by treatment as appropriate. The change from BL in the 24-h urinary calcium and phosphorus excretion will be descriptively summarized by treatment and visit for a subset of subjects participating in the PK analysis.

End of Study Analysis

All safety analyses will be performed for subjects in the SAF who enter Epoch 4.

AEs

The number and percentage of subjects having AEs, SAEs, AEs leading to study medication permanent discontinuation and other significant AEs occurred during Epoch 4 will be summarized and presented by treatment. Similar summaries will be provided for events occurred during the overall 48 weeks of Epoch 3 plus Epoch 4. The AEs of interest, including those related to potential/identified risks as specified in the DSPP, will be summarized as appropriate separately.

Laboratory Data, Vital Signs and ECG

Descriptive summary statistics including for the change from Week 24 to each post-Week 24 study visit during Epoch 4 will be presented by treatment group for each parameter, as well as for the maximum change from BL. In addition, shift tables will be provided for all parameters with available ranges to compare a subject's Week 24 laboratory evaluation relative to the most extreme post-Week 24 value. The change from Week 24 in the 24-h urinary calcium and phosphorus excretion will be descriptively summarized by treatment and visit (for post-Week 24 visits only) for a subset of subjects participating in the PK analysis.

PK

The following PK parameters will be determined using the actual recorded sampling times and non-compartmental method(s) with Phoenix WinNonlin (Version 6.2 or higher): maximum concentration observed (Cmax), maximum time (Tmax), last non-zero concentration area under the curve (AUClast), AUC0-t. Additional PK parameters may be calculated as appropriate. The linear trapezoidal rule will be used for AUC calculation. Descriptive summary statistics will be provided by treatment and visit/sampling time point. Summary statistics will include mean (arithmetic and geometric), SD, CV (arithmetic and geometric), median, minimum and maximum. An exception to this is Tmax where median, minimum and maximum will be presented. Concentrations below the lower limit of quantification (LLOQ) will be treated as zero in summary statistics and for PK parameter calculations. A geometric mean will not be reported if the dataset includes zero values. Individual LIK066 plasma concentration data will be listed by treatment, subject, and visit/sampling time point. PK parameters will also be listed by treatment and subject.

Biomarkers

Week 24 Analysis

Summaries of absolute values and change from BL in each of the bone, renal and inflammatory biomarkers by treatment group and visit will be presented using statistics: n, mean, SD, median, minimum, maximum, Q1, Q3, geometric mean and coefficient of variation. Figures will be produced to visually show the mean values by visit over 24 weeks of treatment in Epoch 3 for each treatment group.

End of Study Analysis

The absolute values and change from Week 24 in each of the bone, renal and inflammatory biomarkers will be similarly summarized and depicted as for the Week 24 analysis.

Analysis of Exploratory Variables

Week 24 Analysis

Data collected from the GSRS questionnaire will be presented for each of the five dimensions descriptively (mean, median, standard deviation, Q1, Q3, minimum and maximum) by treatment and visit (up to and including Week 24 visit). In addition, for each patient the information for the separate dimensions will be combined into one overall score by averaging the dimension scores (provided a mean score is available for all dimensions). Summary statistics: mean, median, standard deviation, Q1, Q3, minimum and maximum for the change form BL in the overall score will be presented by treatment group and visit (up to and including Week 24 visit). The absolute value and change from BL in EQ-5D-5L visual analogue scale will be descriptively summarized (mean, median, standard deviation, Q1, Q3, minimum and maximum) by treatment and visit (up to and including Week 24 visit). The number and percentage of patients in each category (e.g. no problems, some problems, and severe problems) will be provided by treatment and visit, for each dimension (mobility, self-care, usual activities, pain/discomfort and anxiety/depression). The number and percentage of patients in each category (from 'not all difficult', 'slightly difficult' to 'unable to do') will be presented by treatment and visit (up to and including Week 24 visit) for seven questions from APPADL questionnaire separately. In addition, for each patient the information for the seven separate questions will be combined into one overall score by averaging the available scores from the APPADL. Summary statistics: mean, median, standard deviation, Q1, Q3, minimum and maximum for the change form BL in the overall score will be presented by treatment group and visit (up to and including Week 24 visit). For patient reported outcome (PRO) variables related to GSRS, EQ-5D-5L and APPADL questionnaires, BL is defined as the value collected at randomization visit (Week 0). All exploratory analyses will be performed on the FAS only.

End of Study Analysis

To assess the potential effect of the doses used in Epoch 3 on the efficacy and tolerability of the doses subjects used in Epoch 4, the following analyses will be performed: A graphic presentation of raw means over time during the entire 48 week treatment period for each of selected efficacy variables by the 10 individual Epoch 3/Epoch 4 treatment groups. The above graphs may be provided by strata of glycemic status (normoglycemic, dysglycemic and T2DM). Key safety data including selected AEs of interest (eg diarrhea) and key laboratory parameters may be summarized and presented by the 10 individual Epoch 3/Epoch 4 treatment groups. Further analyses using a different treatment grouping strategy, such as pooling the Epoch 3 low doses (eg 2.5 mg qd and 10 mg qd) while keeping all other doses separate to be combined with individual Epoch 4 doses, may be further explored. In addition, the PRO data collected from the GSRS, EQ-5D-5L and APPADL questionnaires during the maintenance period will be similarly analyzed as for Week 24 analysis.

Sample Size Calculation

The study planned to randomize approximately 432 subjects in total, allocated in the ratio of 1:1:1:1:1:2:1:1:1:2 to the following ten Epoch 3/Epoch 4 treatment groups: 1. placebo/placebo; 2. placebo/LIK066 25 mg qd; 3. LIK066 2.5 mg qd/25 mg qd; 4. LIK066 10 mg qd/25 mg qd; 5. LIK066 50 mg qd/25 mg qd; 6. LIK066 150 mg qd/25 mg qd; 7. LIK066 2.5 mg bid/35 mg qd; 8. LIK066 5 mg bid/35 mg qd; 9. LIK066 25 mg bid/35 mg qd; and 10. LIK066 50 mg bid/35 mg qd. This randomization scheme implies that the Epoch 3 treatment and Epoch 4 treatment for a specific subject is determined simultaneously at randomization visit. The randomization will be stratified by subjects' glycemic status at screening: normoglycemic, dysglycemic and T2DM.

As the dose-response assessment is conducted in qd and bid regimens separately (while an overall family-wise type I error is controlled at a one-sided significance level of 2.5%), power calculation was done for testing dose-response signal by regimen as well. FIG. 15 summarizes the average power and the lowest power across the candidate dose response shapes in FIG. 14 by regimen, under different scenarios with the assumptions on effect size of body weight loss (percent change from BL) for the dose of maximum effect, and the related standard deviations.

Note that a dose-response signal is detected (i.e. the primary objective is met) as long as either of the dose-response signals for the two regimens is detected. Therefore, the overall study power is at least the maximum of the powers between two regimens for each scenario considered. It was assumed that the effect of losses to follow-up is equivalent to effectively having 15% fewer subjects than randomized, even if the multiple imputation approach used to handle missing values should be able to recover some information for such subjects.

Regulatory and Ethical Compliance

This clinical study was designed and shall be implemented, executed and reported in accordance with the International Conference on Harmonization of Technical Requirements for Registration of Pharmaceuticals for Human Use (ICH) Harmonized Tripartite Guidelines for Good Clinical Practice, with applicable local regulations (including European Directive 2001/20/EC, United States (US) CFR 21, and Japanese Ministry of Health, Labor, and Welfare), and with the ethical principles laid down in the Declaration of Helsinki.

Informed Consent Procedures

Eligible subjects may only be included in the study after providing written (witnessed, where required by law or regulation), IRB/IEC-approved informed consent, or, if incapable of doing so, after such consent has been provided by a legally acceptable representative(s) of the subject. In cases where the subject's representative gives consent, the subject must be informed about the study to the extent possible given his/her understanding. If the subject is capable of doing so, she/he must indicate assent by personally signing and dating the written ICF or a separate assent form. Informed consent must be obtained before conducting any study-specific procedures (e.g. all of the procedures described in the protocol). The process of obtaining informed consent must be documented in the subject source documents.

Novartis will provide to investigators in a separate document a proposed ICF that complies with the ICH GCP guidelines and regulatory requirements and is considered appropriate for this study. Any changes to the proposed ICF suggested by the investigator must be agreed to by Novartis before submission to the IRB/IEC and a copy of the approved version must be provided to the Novartis monitor after IRB/IEC approval.

Women of child bearing potential must be informed that taking the study treatment may involve unknown risks to the fetus if pregnancy were to occur during the study and agree that in order to participate in the study they must adhere to the contraception requirement for the duration of the study. If there is any question that the subject will not reliably comply, they must not be entered in the study.

Responsibilities of the Investigator and IRB/IEC

Before initiating a study, the investigator/institution must obtain approval/favorable opinion from the IRB/IEC for the study protocol, written ICF, consent form updates, subject recruitment procedures (eg, advertisements) and any other written information to be provided to subjects. Prior to study start, the investigator is required to sign a protocol signature page confirming her/his agreement to conduct the study in accordance with these documents and all of the instructions and procedures found in this protocol and to give access to all relevant data and records to Novartis monitors, auditors, Novartis Quality Assurance representatives, designated agents of Novartis, IRBs/IECs, and regulatory authorities as required. If an inspection of the clinical site is requested by a regulatory authority, the investigator must inform Novartis immediately that this request has been made.

Quality Control and Quality Assurance

Novartis maintains a robust Quality Management system that includes all activities involved in quality assurance and quality control, including the assignment of roles and responsibilities, the reporting of results, and the documentation of actions and escalation of issues identified during the review of quality metrics, incidents, audits and inspections. Audits of investigator sites, vendors, and Novartis systems are performed by Novartis Pharma Auditing and Compliance Quality Assurance, a group independent from those involved in conducting, monitoring or performing quality control of the clinical study. The clinical audit process uses a knowledge/risk based approach. Audits are conducted to assess GCP compliance with global and local regulatory requirements, protocols and internal standard operation procedures, and are performed according to written Novartis processes.

Protocol Adherence

This protocol defines the study objectives, the study procedures and the data to be collected on study participants. Additional assessments required to ensure safety of subjects should be administered as deemed necessary on a case by case basis. Under no circumstances is an investigator allowed to collect additional data or conduct any additional procedures for any research related purpose involving any investigational drugs under the protocol. Investigators ascertain they will apply due diligence to avoid protocol deviations. If an investigator feels a protocol deviation would improve the conduct of the study this must be considered a protocol amendment, and unless such an amendment is agreed upon by Novartis and approved by the IRB/IEC and health authorities, where required, it cannot be implemented.

Protocol Amendments

Any change or addition to the protocol can only be made in a written protocol amendment that must be approved by Novartis, health authorities where required, and the IRB/IEC prior to implementation. Only amendments that are intended to eliminate an apparent immediate hazard to subjects may be implemented immediately provided the health authorities are subsequently notified by protocol amendment and the reviewing IRB/IEC is notified.

Notwithstanding the need for approval of formal protocol amendments, the investigator is expected to take any immediate action required for the safety of any subject included in this study, even if this action represents a deviation from the protocol. In such cases, the reporting requirements identified infra must be followed.

Preliminary Results

The following table shows the results of the dose response signal for the percentage change in body weight over the course of the above described study. The term "test statistics" indicates the analytical fit for the modeling described above. The higher the test statistic, the better the fit. Values over 5 are generally good predictors of efficacy of a particular dosing regimen.

As seen in the table below, there is a clear dose response signal as shown in the test statistic for both the once daily (q.d.) and the twice daily (b.i.d.) dosages. From the data below, it appears that 50 mg qd and bid regimens are especially responsive.

TABLE 1

Dose-response signal for % change in body weight (kg) at Week 24 FAS

| Model | Test statistics | Adjusted p-value |
|---|---|---|
| Candidate models for qd regimen | | |
| Emax ED50 = 5 mg | 5.396 | <0.0001 |
| Emax ED50 = 50 mg | 5.546 | <0.0001 |
| Sigmoid Emax ED50 = 75 mg h = 3.5 | 5.109 | <0.0001 |
| Sigmoid Emax ED50 = 25 mg h = 0.7 | 5.606 | <0.0001 |
| Beta Model | 5.500 | <0.0001 |
| Exponential | 5.132 | <0.0001 |
| Candidate models for bid regimen | | |
| Emax ED50 = 5 mg | 5.738 | <0.0001 |
| Emax ED50 = 50 mg | 5.833 | <0.0001 |
| Sigmoid Emax ED50 = 75 mg h = 3.5 | 4.970 | <0.0001 |
| LinLog Model | 5.884 | <0.0001 |
| Linear | 5.431 | <0.0001 |
| Quadratic | 5.852 | <0.0001 |

The invention claimed is:

1. A method of treating obesity, comprising administering to a patient in need, a dosage of about 1-50 mg of LIK066, or salt thereof; wherein said patient has a body mass index of at least 25 kg/m$^2$.

2. The method according to claim 1, wherein the dosage is selected from the group consisting of 2.5 mg, 5 mg, 10 mg, 25 mg, 35 mg, and 50 mg.

3. The method according to claim 1, wherein the dosage is about 35 mg.

4. The method according to claim 1, wherein the dosage is about 50 mg.

5. The method of claim 1, wherein said LIK066 or salt thereof is formulated for oral administration.

6. The method according to claim 1, wherein the dosage is administered once a day.

7. The method according to claim 1, wherein the dosage is administered twice a day.

8. The method of claim 1, wherein said patient has a condition associated with obesity selected from high blood pressure, high levels of triglycerides, elevated fasting blood glucose and diabetes.

9. The method of claim 1, wherein said patient has a body mass index of at least 30 kg/m$^2$.

10. The method of claim 1, comprising a reduction of at least about 5% of body weight.

11. A method of treating obesity, comprising administering to a patient, a dosage of about 35-50 mg of LIK066 or a salt thereof once or twice daily; wherein said patient has a body mass index of at least 25 kg/m$^2$.

12. The method of claim 11, comprising administering about 50 mg of LIK066 or a salt thereof.

13. The method of claim 11, wherein said patient has a condition associated with obesity selected from high blood pressure, high levels of triglycerides, elevated fasting blood glucose and diabetes.

14. The method of claim 11, wherein said patient has a body mass index of at least 30 kg/m$^2$.

15. The method of claim 11, comprising a reduction of at least about 5% of body weight.

\* \* \* \* \*